(12) United States Patent
Ueda et al.

(10) Patent No.: US 7,039,458 B2
(45) Date of Patent: May 2, 2006

(54) BODY FAT MEASURING SYSTEM FOR PREGNANT WOMAN AND HEALTH CARE SYSTEM FOR PREGNANT WOMAN

(75) Inventors: Yasuo Ueda, Sasayama (JP); Motoyoshi Maruo, Hyogo (JP); Yoshihiko Ashitaka, Ashiya (JP); Yuka Honda, Tokyo (JP); Yuko Kitahara, Niiza (JP)

(73) Assignee: Tanita Corporation, Tokyo (JP)

( * ) Notice: Subject to any disclaimer, the term of this patent is extended or adjusted under 35 U.S.C. 154(b) by 645 days.

(21) Appl. No.: 10/200,256

(22) Filed: Jul. 23, 2002

(65) Prior Publication Data
US 2003/0023186 A1   Jan. 30, 2003

(30) Foreign Application Priority Data
Jul. 24, 2001   (JP)   ............................. 2001-223536
Jul. 24, 2001   (JP)   ............................. 2001-223537
Apr. 4, 2002    (JP)   ............................. 2002-102210

(51) Int. Cl.
*A61B 5/05*   (2006.01)
(52) U.S. Cl. ..................................................... 600/547
(58) Field of Classification Search ................ 600/547, 600/551, 587; 177/25.12, 25.19; 128/920
See application file for complete search history.

(56) References Cited

U.S. PATENT DOCUMENTS

| | | | |
|---|---|---|---|
| 5,086,781 A * | 2/1992 | Bookspan | ..................... 600/547 |
| 6,256,532 B1 | 7/2001 | Cha | |
| 6,369,338 B1 * | 4/2002 | Kimura | ...................... 600/551 |
| 6,434,422 B1 * | 8/2002 | Tomoda et al. | ............. 600/547 |

FOREIGN PATENT DOCUMENTS

| | | |
|---|---|---|
| EP | 1063500 A2 | 12/2000 |
| EP | 1076230 A1 | 1/2001 |
| EP | 1080687 A1 | 3/2001 |
| WO | WO 99/52425 | 10/1999 |

* cited by examiner

OTHER PUBLICATIONS

Henry C. Lukaski et al., "Total body water in pregnancy: assessment by using bioelectrical impedance[1-3]", American Journal of Clinical Nutrition, Bethesda, MD, US, vol. 59, No. 3, Mar. 1994, pp. 578-585, XP-000965432.

*Primary Examiner*—Eric F. Winakur
(74) *Attorney, Agent, or Firm*—McDermott Will & Emery LLP

(57) ABSTRACT

Measurements by use of a conventional caliper process require skills and experiences. Further, since different pregnant women gain and keep fats in their bodies in different ways, results of measurements of their body fats vary. To overcome the inconvenience, there is provided a system for measuring a percent body fat or a total body fat by a bioelectrical impedance method, which comprises first input means, second input means and computation means, wherein personal data of a patient such as a height and a body weight is input into the first input means, a weight of a fetal part is input into the second input means, and the computation means computes a percent body fat or a total body fat by subtracting the body weight input into the second input means from the body weight input into the first input means. Further, to overcome the inconvenience, there is provided a system for measuring a percent body fat by a bioelectrical impedance method which comprises first input means, second input means and computation means, wherein personal data of a patient such as a height and a body weight is input into the first input means, a weight of a fetal part is input into the second input means, and the computation means computes a percent body fat by subtracting the body weight input into the second input means from the body weight input into the first input means.

27 Claims, 22 Drawing Sheets

FIG. 5

| | | |
|---|---|---|
| MEASURING DATE AND TIME: 6/1/2001, 10:27' A.M. | | |
| GENDER/BODY TYPE MODE | | MALE/STANDARD |
| AGE | | 35 YEARS |
| HEIGHT | | 168.0 cm |
| BODY WEIGHT | | 63.4 kg |
| IMPEDANCE | | 525 Ω |
| PERCENT BODY FAT | | 26.2 % |
| TOTAL BODY FAT | | 16.6 kg |
| FAT-FREE BODY WEIGHT | | 46.8 kg |
| TOTAL BODY WATER | | 34.2 kg |
| BMI | | 23.9 |

FIG. 7

| MEASURING DATE AND TIME: 6/1/2001, 10:27' A.M. | | |
|---|---|---|
| GENDER/BODY TYPE MODE | | MATERNITY |
| GESTATIONAL WEEKS | | 24 WEEKS 5 DAYS |
| AGE | | 35 YEARS |
| HEIGHT | | 159.0 cm |
| PRE-CORRECTION AND POST-CORRECTION BODY WEIGHTS | 54.0 kg | 52.0 kg |
| FETAL BODY WEIGHT | | 1.201 kg |
| WEIGHT OF AMNIOTIC FLUID | | 0.534 kg |
| WEIGHT OF PLACENTA | | 0.265 kg |
| IMPEDANCE | | 580 Ω |
| PERCENT BODY FAT | | 21.3 % |
| TOTAL BODY FAT | | 11.1 kg |
| FAT-FREE BODY WEIGHT | | 40.9 kg |
| TOTAL BODY WATER | | 29.9 kg |
| PRE-CORRECTION BMI | | 21.4 |

FIG. 13

AMOUNT OF INCREASE IN BODY FAT PER WEEK FOR EACH BODY TYPE ALONG WITH INCREASE IN GESTATIONAL WEEKS

UNIT: g

| GESTATIONAL WEEKS | ~19 | 20~23 | 24~27 | 28~31 | 32~35 | 36~39 |
|---|---|---|---|---|---|---|
| SLIM | 210 | 170 | 110 | 5 | 80 | 40 |
| NORMAL | 130 | 205 | 130 | 45 | 90 | 5 |
| OBESE | 60 | 170 | 10 | -10 | -20 | -50 |

FIG. 19

| TBW/FAT<br>RATE OF<br>CHANGE | WITHIN APPROPRIATE RANGE | BETWEEN UPPER LIMITS OF APPROPRIATE RANGE AND a | HIGHER THAN a |
|---|---|---|---|
| LOWER THAN 0 | 0 | 1 | 2 |
| BETWEEN 0 AND b | 1 | 2 | 3 |
| HIGHER THAN b | 2 | 3 | 4 |

BODY FAT MEASURING SYSTEM FOR PREGNANT WOMAN AND HEALTH CARE SYSTEM FOR PREGNANT WOMAN

BACKGROUND OF THE INVENTION

1. Field of the Invention

The present invention relates to a system for measuring a body fat, particularly a system for measuring a body fat of a pregnant woman and also a system for administrating health of a pregnant woman, particularly a system for administrating health of a pregnant woman with respect to edema and toxemia of pregnancy.

2. Description of the Related Art

From the viewpoint of ages, a conventional body fat measuring device is capable of measuring body fats of subjects ranging from children to elderly people. However, it is not capable of measuring body fats of pregnant women. Meanwhile, an examiner can see an alteration in fats of a pregnant woman by observing an alteration in subcutaneous fats by an ultrasonic adipometer, a caliper or the like. However, measurements by use of a conventional caliper process require skills and experiences. Further, the distribution of fat was different by each pregnant woman. Therefore, results of measurements of their body fats vary.

In addition, heretofore, to determine onset of edema of a pregnant woman, it has been checked whether an impression is made and left when tibia is pressed with a thumb. Lower extremities of the pregnant woman shows edema of pregnancy toxemias. And this pregnant woman is diagnosed with slight pregnancy toxemias that body weight of the pregnant woman which appeared of edema increases more than 500 g in one week. Furthermore, this pregnant woman is diagnosed as severe toxemia of pregnancy when this edema extends to a whole body of pregnant woman. However, determination of onset of edema is apt to be dependent on subjectivity of a doctor who diagnoses a patient, and its quantitative determination has heretofore been impossible. Further, it is known that an increase in body weight also varies greatly according to an intake of food, an amount of excrement and an amount of sweat on a day and a body weight can be increased or decreased by about 500 g soon.

SUMMARY OF THE INVENTION

It is a primary object of the present invention to provide a system for measuring a body fat of a pregnant woman.

It is another object of the present invention to provide a system for measuring a body fat percent of a pregnant woman.

It is a further object of the present invention to provide a system for measuring a body fat weight of a pregnant woman.

It is a still further object of the present invention to provide a system for measuring a percent body fat or total body fat of a pregnant woman by a bioelectrical impedance method, which comprises first input means, second input means and computation means, wherein personal data of a subject such as a height and a body weight is input into the first input means, a weight of a fetal part is input into the second input means, and the computation means computes a percent body fat or total body fat by subtracting the body weight input into the second input means from the body weight input into the first input means.

It is a still further object of the present invention to provide a system for measuring a percent body fat or total body fat of a pregnant woman by a bioelectrical impedance method, which comprises first input means, second input means, computation means and determination means, wherein personal data of a subject such as a height and a body weight is input into the first input means, a weight of a fetal part is input into the second input means, the computation means computes a percent body fat or total body fat by subtracting the body weight input into the second input means from the body weight input into the first input means, and the determination means determines the percent body fat or total body fat based in gestational weeks.

It is a still further object of the present invention to provide a system for measuring a percent body fat or total body fat of a pregnant woman by a bioelectrical impedance method, which comprises first input means, second input means, computation means and determination means, wherein personal data of a subject such as a height and a body weight is input into the first input means, a weight of a fetal part is input into the second input means, the computation means computes a percent body fat or total body fat by subtracting the body weight input into the second input means from the body weight input into the first input means, and the determination means determines the percent body fat or total body fat based on a length of uterine fundus.

It is a still further object of the present invention to provide a system for measuring a percent body fat or total body fat of a pregnant woman by a bioelectrical impedance method, which comprises first input means, second input means, computation means and determination means, wherein personal data of a subject such as a height and a body weight is input into the first input means, a weight of a fetal part is input into the second input means, the computation means computes a percent body fat or total body fat by subtracting the body weight input into the second input means from the body weight input into the first input means, and the determination means determines the percent body fat or total body fat based on a fetal body weight.

According to one embodiment of the present invention, a weight of a fetal part which is determined from the gestational weeks is input into the second input means.

According to another embodiment of the present invention, a weight of a fetal part which is determined from a length of uterine fundus is input into the second input means.

According to another embodiment of the present invention, a weight of a fetal part which is determined by ultrasonotomography is input into the second input means.

According to another embodiment of the present invention, a weight of a fetal part which is determined from the gestational weeks and a length of uterine fundus is input into the second input means.

According to another embodiment of the present invention, a weight of a fetal part which is determined from the gestational weeks and by ultrasonotomography is input into the second input means.

According to another embodiment of the present invention, a weight of a fetal part which is determined from a length of uterine fundus and by ultrasonotomography is input into the second input means.

According to another embodiment of the present invention, the weight of the fetal part comprises a fetal body weight, a weight of an amniotic fluid and a weight of a placenta.

It is a still further object of the present invention to provide a health care system for a pregnant woman, which comprises input means, computation means, reference setting means, comparison means and determination means, wherein personal data of a pregnant woman such as a height and a body weight is input into the input means, the computation means computes a total body water and a total body fat by a bioelectrical impedance method, the reference setting means has reference values corresponding to a specific week after conception, the comparison means compares the results of the computations performed by the computation means with the reference values, and the determination means determines a physical condition of the pregnant woman based on the results of the comparisons made by the comparison means.

According to one embodiment of the present invention, the determination means determines onset of edema.

According to one embodiment of the present invention, the determination means determines onset of toxemia of pregnancy.

According to one embodiment of the present invention, the determination means determines onsets of edema and toxemia of pregnancy.

According to one embodiment of the present invention, the determination means displays advice about health of the pregnant woman.

According to one embodiment of the present invention, the computation means computes the total body water and the total body fat based on a bioelectrical impedance between feet of the pregnant woman.

It is a still further object of the present invention to provide a health care system for a pregnant woman, which comprises input means, computation means, reference setting means, comparison means and determination means, wherein personal data of a pregnant woman such as a height and a body weight is input into the input means, the computation means computes a ratio of a total body water to a total body fat by a bioelectrical impedance method, the reference setting means has a reference ratio value corresponding to a specific week after conception, the comparison means compares a rate of change from the ratio computed by the computation means with the reference ratio value, and the determination means determines a physical condition of the pregnant woman based on the result of the comparison made by the comparison means.

According to one embodiment of the present invention, the determination means determines onset of edema when the computed ratio is larger than the reference ratio value.

According to one embodiment of the present invention, the determination means determines onset of toxemia of pregnancy when the computed ratio is larger than the reference ratio value.

According to one embodiment of the present invention, the determination means determines onsets of edema and toxemia of pregnancy when the computed ratio is larger than the reference ratio value.

According to one embodiment of the present invention, the determination means displays advice about health of the pregnant woman.

According to one embodiment of the present invention, the computation means computes the total body water and the total body fat based on a bioelectrical impedance between feet of the pregnant woman.

According to one embodiment of the present invention, the reference setting means uses, as the reference ratio value, a ratio value corresponding to a specific week after conception during which the bioelectrical impedance of the pregnant woman is stable.

BRIEF DESCRIPTION OF THE DRAWINGS

FIG. 5 is a diagram showing an example of a printout in a mode other than a maternity mode.

FIG. 7 is a diagram showing an example of a printout in the maternity mode.

FIG. 13 is a diagram showing the gestational weeks and amounts of increase in body fat.

FIG. 19 is a diagram showing an example of criteria for determining levels of developments of edema and toxemia of pregnancy, the criteria resulting from combining possible results of determination of the TBW/FAT ratio and possible results of determination of the rate of change.

DETAILED DESCRIPTION OF THE PREFERRED EMBODIMENT

Figure 1:
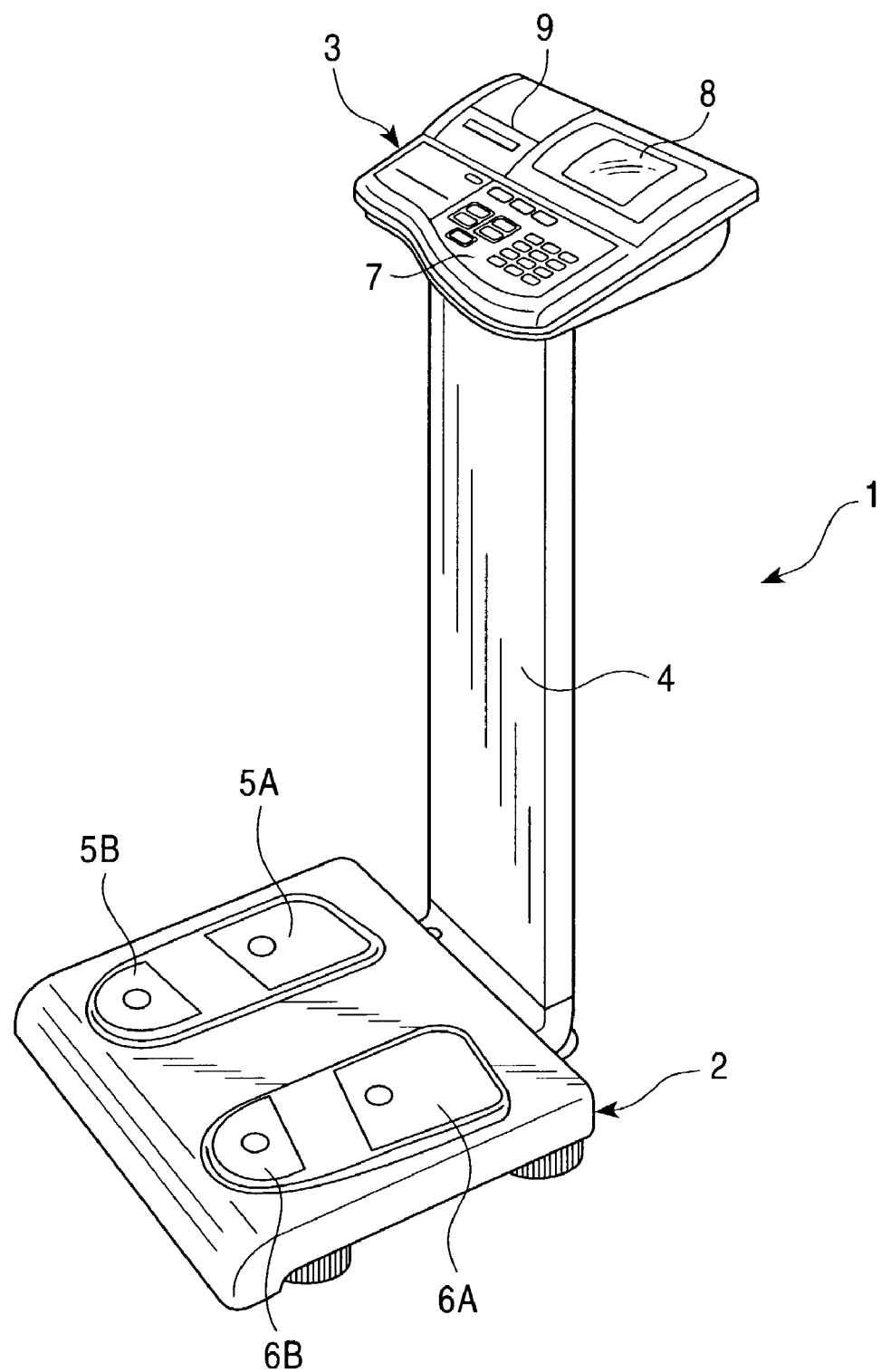
FIG. 1 is an external oblique perspective view of a first embodiment of the present invention.

A first embodiment of the present invention will be described with reference to the drawings. FIG. 1 is an external oblique perspective view of a system 1 according to the present invention which can be used as a percent body fat measuring system for a pregnant woman and also a health care system for a pregnant woman. The system 1 roughly comprises a measuring section 2, a display/print section 3, and a support 4 which is fixed to a base plate for the measuring section 2 which is not shown and to the display/print section 3.

The measuring section 2 has the same constitution as that of a known body fat measuring device. The section 2 has a body weight measuring sensor therein and can measure a body weight of a patient when the patient stands on a top surface of the measuring section 2. In addition, on the top surface of the measuring section 2, electric current supplying electrodes 5A and 6A and voltage measuring electrodes 5B and 6B are provided so as to measure a bioelectrical impedance between feet.

Meanwhile, the display/print section 3, as shown in FIG. 1, comprises an operating section 7, a display section 8 for displaying input data and results of measurements, and a print section 9 for printing results of measurements.

Figure 2:
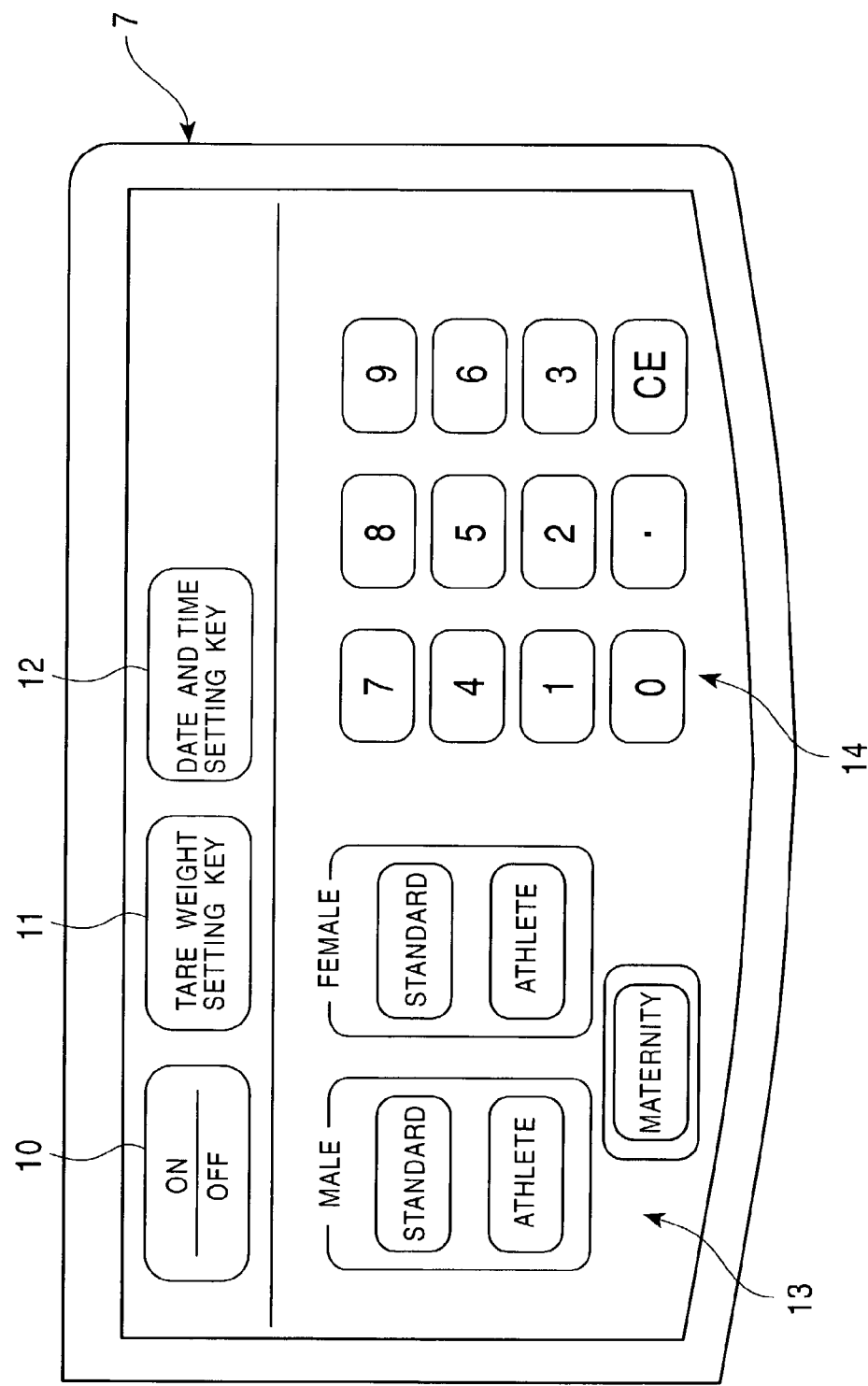
FIG. 2 is a diagram showing a display/print section of the first embodiment of the present invention.

The operating section 7 in FIG. 2 comprises a power switch 10, a tare weight setting key 11 for setting a weight of clothing of a patient, a key 12 for setting a date and time, a group of keys 13 for setting a gender and a body type, and a numeric keypad 14 for entering data and the like.

Figure 3:
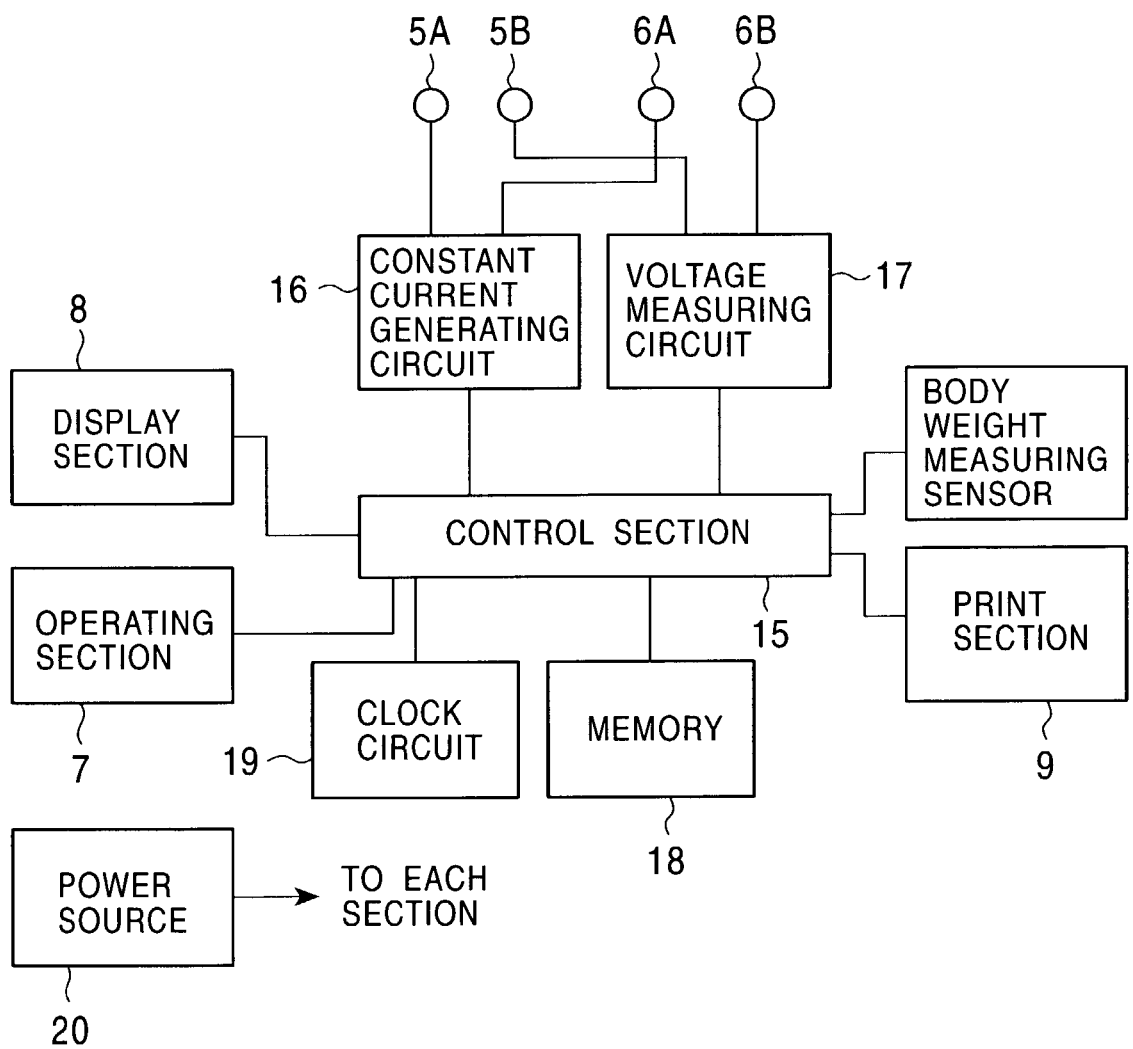
FIG. 3 is an electric block diagram.

FIG. 3 is an electric block diagram of the system 1 for a pregnant woman. The system 1 has a control section 15 which has a microcomputer therein. To the control section 15, the switch and keys in the operating section 7 in FIG. 2 as well as the display section 8 and the print section 9 are connected.

As for the measuring section 2, the electric current supplying electrodes 5A and 6A are connected to the control circuit 15 via a constant current generating circuit 16, the voltage measuring electrodes 5B and 6B are connected to the control circuit 15 via a voltage measuring circuit 17, and the body weight measuring sensor is also connected to the control circuit 15.

In addition, a memory 18 for storing data as well as a clock circuit 19 for generating date and time data such as the gestational weeks is also connected to the control circuit 15.

A power source 20 supplies power to these sections.

Next, operations of the system 1 for a pregnant woman according to the present invention will be described with reference to a flowchart shown in FIG. 4. First of all, when the power switch 10 is pressed to be ON, the control circuit 15 initializes the microcomputer, the memory 18 and the like in STEP S1. Then, in STEP S2, the system 1 determines whether a date and time is already set. If it is already set, the system 1 proceeds to STEP S4. If it is not set yet, it is set in STEP S3. A detailed description of the setting of the date and time will be omitted since it is carried out in the same manner as in a commonly used device.

In STEP S4, a message "Enter a weight of your clothing or a tare weight using the numeric keypad 14. Press the tare weight setting key 11 when you are done." is displayed on the display section 8. Then, if an patient enters "1.0 kg" by use of the numeric keypad 14 and presses the tare weight setting key 11, the action is determined to be "Yes" in STEP S5, and the system 1 proceeds to STEP S6 where the tare weight is stored in the memory 18. If the tare weight setting key 11 is not pressed in STEP S5, the system 1 returns to STEP S4 so as to display the message urging the patient to enter the tare weight again.

Then, in STEP S7, a message urging the patient to press a key which matches the patient among the keys 13 for setting a gender and a body type is displayed on the display section 8. For example, when the patient is a standard male, the patient presses a "STANDARD" key in a box marked as "MALE" in FIG. 2. Then, the input is detected in STEP S8, and the system 1 proceeds to STEP S9 where data corresponding to the pressed key is stored in the memory 18. Until the key is pressed, the system 1 keeps returning to STEP S7 from STEP S8 and urging the patient to press the key.

Similarly, an age of the patient is entered and stored in the memory 18 in STEPS S10 to S12, and a height of the patient is entered and stored in the memory 18 in STEPS S13 to S15.

Then, in STEP S16, it is determined which key has been pressed in STEP S8. In this case, since the patient is a standard male, the key-pressing action is determined to be "No", and the system 1 proceeds to STEP S17.

In STEP S17, the system 1 starts to carry out a measurement after confirming that the patient is standing on the measuring section 2 with his toes in contact with the electric current supplying electrodes 5A and 6A and his heels in contact with the voltage measuring electrodes 5B and 6B. To determine a body weight, an output from the body weight sensor is taken into the control unit 15, and the body weight is calculated in STEP S18. Meanwhile, to determine impedance, a constant current is passed between the electrodes 5A and 6A from the constant current circuit 16, a voltage between the electrodes 5B and 6B is measured by the voltage measuring circuit 17, and the impedance is calculated based on a relationship between the electric current and the voltage in STEP S18. In STEP S18, the tare weight is subtracted from the measured body weight so as to determine the body weight of the patient, a percent body fat is calculated from the impedance, the body weight is multiplied by the percent body fat so as to determine a total body fat, the total body fat is subtracted from the body weight so as to determine a fat-free body weight, the fat-free body weight is multiplied by 73.2%, which is an average percent body water, so as to determine a total body water, and BMI (Body Mass Index) is calculated from the height and the body weight. Then, the results of the calculations are not only displayed on the display section 8 but also printed out from the print section 9 in STEP S19.

FIG. 5 shows an example of the results of the calculations displayed on the display section 8 and the printout. In addition to a measuring date and time, personal data including the input gender, body type, age and height and the results of the measurements and calculations carried out in STEPS S17 and S18 are displayed and printed out.

After displaying and printing out these data, the system 1 returns to STEP S4 and waits for another data entry.

If a "MATERNITY" key is pressed in STEP S8, the key-pressing action is determined to be "YES", and the system 1 proceeds to STEP S20. In STEP S20, a message "Enter your expected date of confinement." is displayed on the display section 8. Until the date is entered by means of the numeric keypad in STEP S21, STEPS S20 and S21 are repeatedly carried out.

When the expected date is entered, the input is determined to be "Yes" in STEP S21, and the gestational weeks is calculated from the expected date of confinement and the data obtained on the measuring date in STEP S22 and stored in the memory 18 in STEP S23.

In a case where the "MATERNITY" key has been pressed, processes to be performed in STEP S17 are the same as those in a case where a key other than the "MATERNITY" key is pressed.

As for data calculations performed in STEP S18, the following calculations are performed in addition to the calculations described above.

Figure 6:
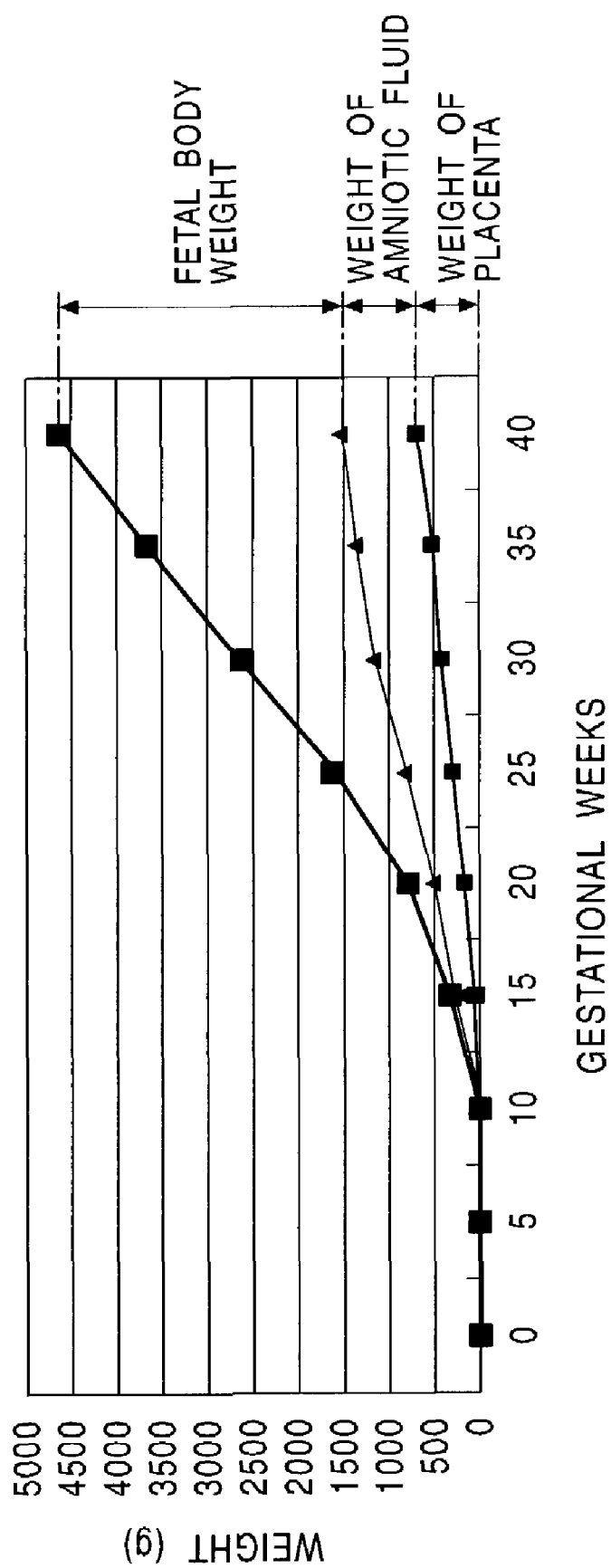
FIG. 6 is a diagram showing a relationship between the gestational weeks and a weight of a fetal part.

Based on graphs (whose data are stored in the memory 18) shown in FIG. 6, a fetal body weight, a weight of an amniotic fluid and a placental weight are read from a specific gestational weeks, and they are subtracted from the measured body weight excluding the tare weight so as to determine a body weight excluding the weight of the fetal part, and based on the body weight, a percent body fat, a total body fat, a fat-free body weight, a total body water, a total body water/total body fat (TBW/FAT) ratio are calculated (Please note that the total body water/total body fat is utilized only when the system 1 is used as the health care system).

Then, the results of the calculations are displayed on the display section 8 and printed out in the print section 9 in STEP S19. An example of the display section and the printout, as shown in FIG. 7, comprises the gestational weeks, a pre-correction body weight (excluding a tare weight) before a weight of a fetal part is subtracted therefrom, a post-correction body weight excluding the weight of the fetal part, a fetal body weight, a weight of an amniotic fluid, a weight of a placenta, a total body water/total body fat ratio and pre-correction BMI determined from the body weight (excluding the tare weight) before the weight of the fetal part is subtracted therefrom and a height in addition to the data in the example of FIG. 5 (Please note that the total body water/total body fat is utilized only when the system 1 is used as the health care system). The reason that the pre-correction BMI is calculated and displayed or printed out is to provide the data to an obstetrician-gynecologist who patient a condition of a growing fetus based on the pre-correction BMI value.

Similarly, for the purpose of data provision, BMI of the patient when she is not pregnant and an amount of increase in body weight determined by subtracting a body weight of the patient when she is not pregnant from the measured pre-correction body weight may be printed or displayed in addition to the example of the printout shown in FIG. 7 or the data displayed on the display 8.

Upon completion of the display and the printout in STEP S19, the system 1 returns to STEP S4 and waits for another data entry.

Figure 8:
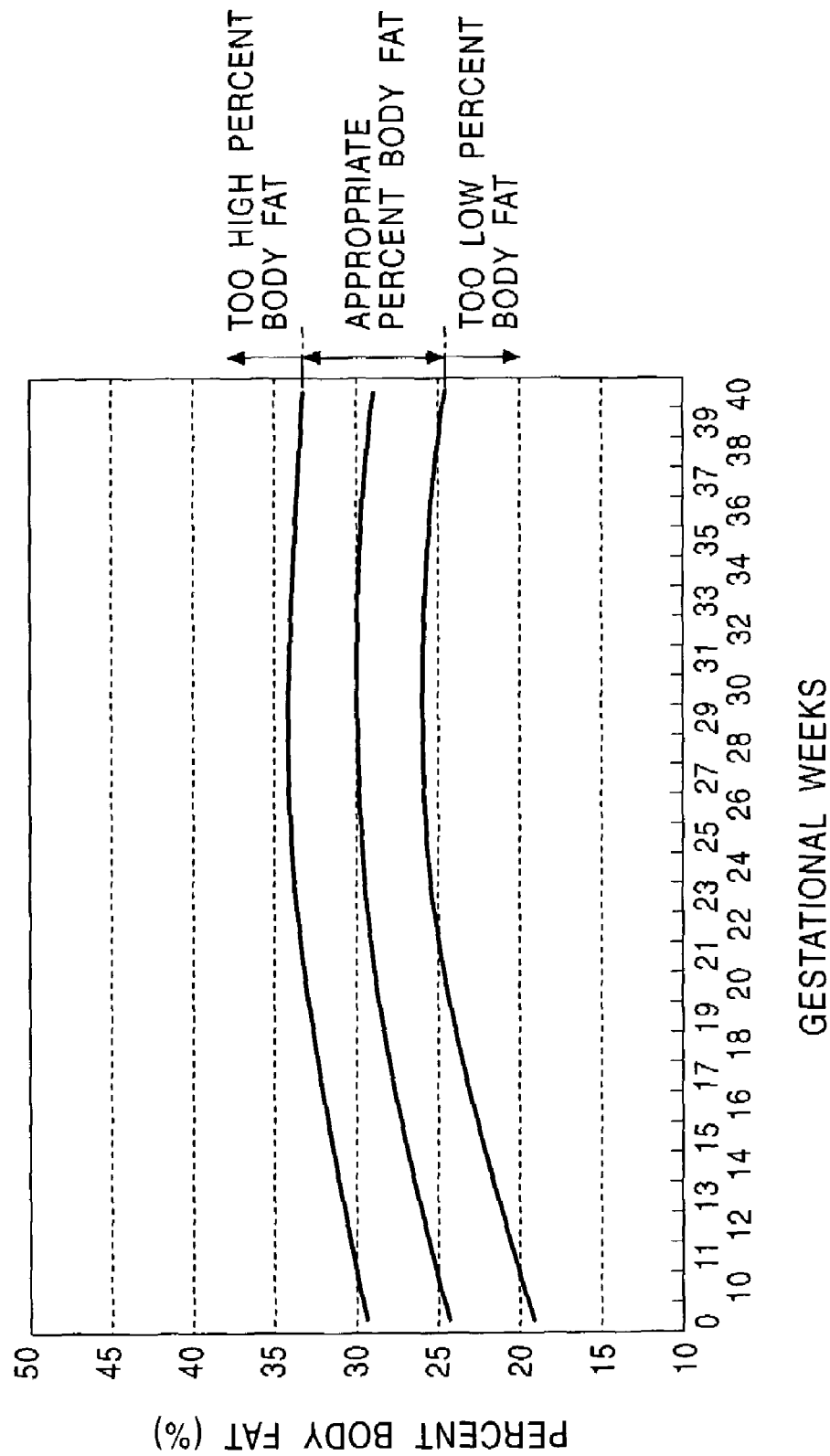
FIG. 8 is a diagram showing a relationship between the gestational weeks and a percent body fat.

In the above data display in the maternity mode, the percent body fat is displayed only in numeric values. Meanwhile, it has heretofore been found that a relationship between the gestational weeks and an appropriate percent body fat is such that in the case of a pregnant woman with a normal figure to be described later, the appropriate percent body fat increases in an early stage of pregnancy and slightly decreases in a late stage of pregnancy as shown in FIG. 8. Therefore, if data of the graph is stored in the memory 18 and it is determined according to the gestational weeks whether the percent body fat is too low, appropriate or too high after calculation of the percent body fat in STEP S18 and some advice based on the determination is displayed or printed, the pregnant woman can find means for improving her physical condition with ease.

Figure 10:
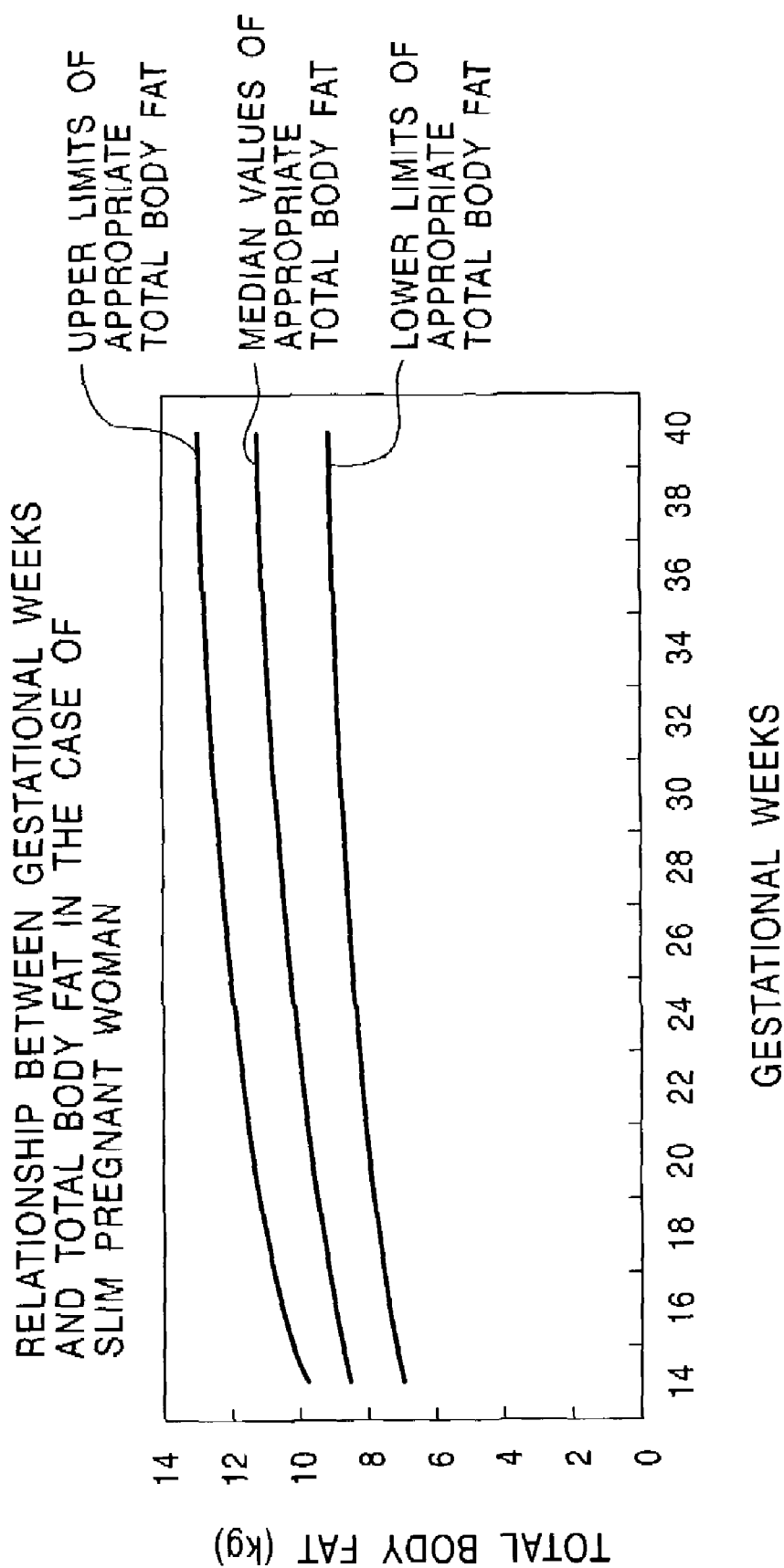
FIG. 10 is a diagram showing a relationship between the gestational weeks and a total body fat of a pregnant woman who is slim.
Figure 11:
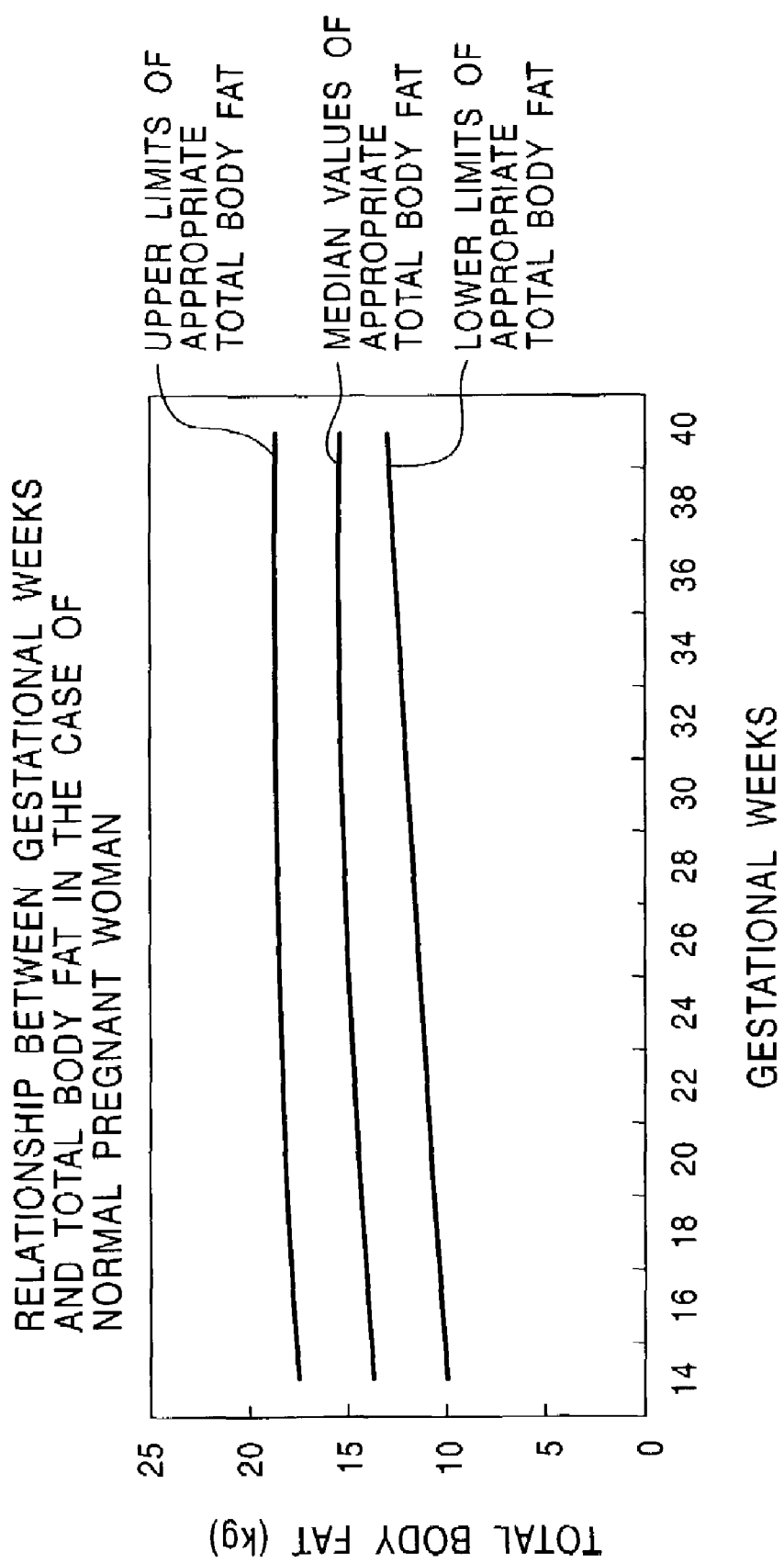
FIG. 11 is a diagram showing a relationship between the gestational weeks and a total body fat of a pregnant woman who is of normal body type.
Figure 12:
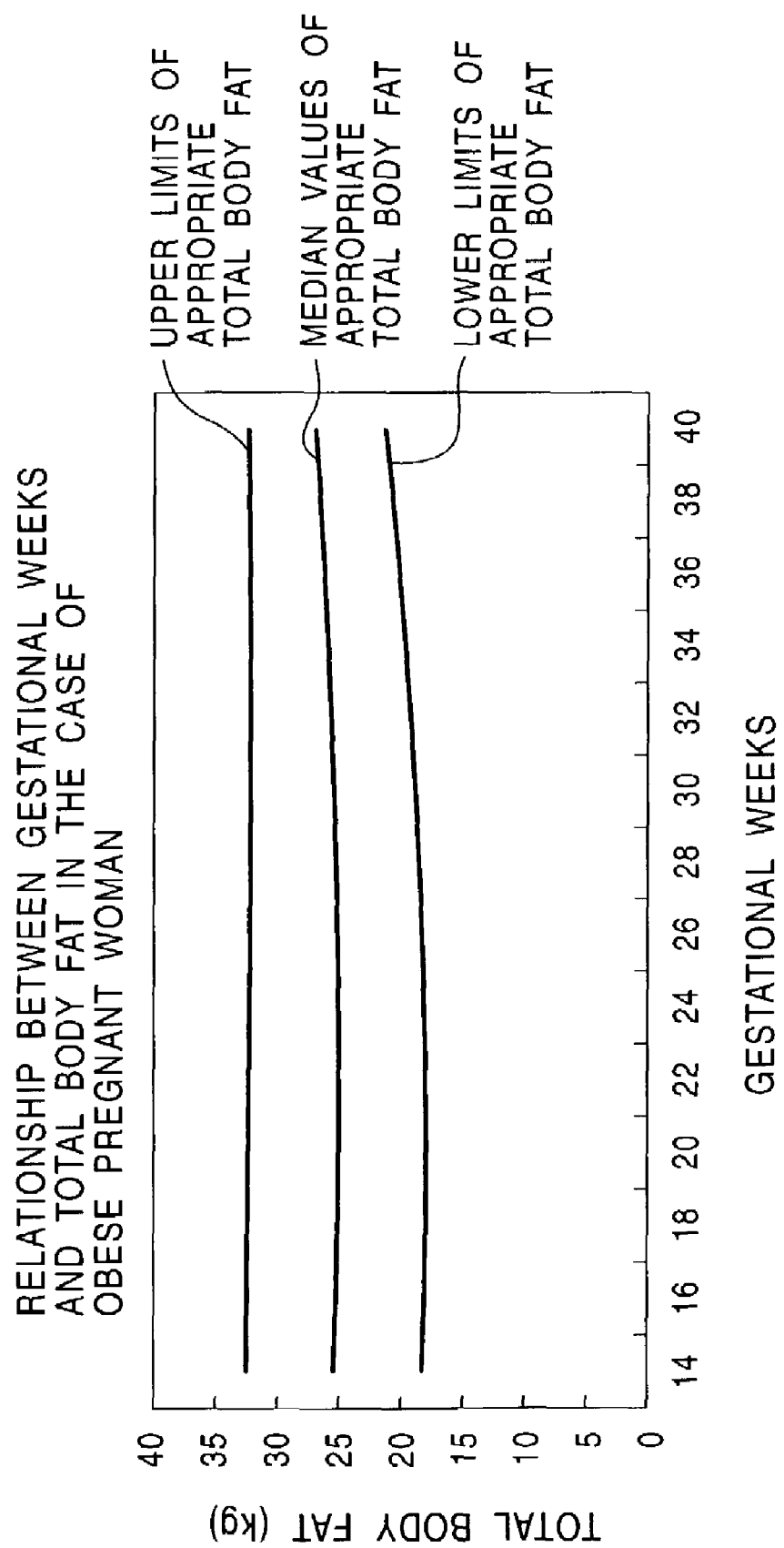
FIG. 12 is a diagram showing a relationship between the gestational weeks and a total body fat of a pregnant woman who is obese.

Further, in the above data display in the maternity mode, the percent body fat has been determined to be too low, appropriate or too high and advice has been made based on the relationship shown in FIG. 8 between the gestational weeks and the percent body fat. Similarly, a total body fat may be determined to be too low, appropriate or too high and appropriate advice may be made based on a relationship between the gestational weeks and the total body fat. In this case, an appropriate range varies as shown in FIGS. 10, 11 and 12 according to whether the subject's body type when she is not pregnant is slim (BMI is lower than 18), normal (BMI is 18 to 24) or obese (BMI is higher than 24). In these figures, a middle graph indicates median values of an appropriate total body fat, an upper graph indicates upper limits of the appropriate total body fat, and a lower graph indicates lower limits of the appropriate total body fat. Therefore, the patient's BMI in non-pregnant state is entered at some point from STEP S7 to STEP S15 in FIG. 4, and when a total body fat value which exceeds the upper graph is measured, advice such as "Your current total body fat is too high. Menus of desirable meals are as follows." is displayed on the display section 8 or printed out in the print section 9.

Figure 4:
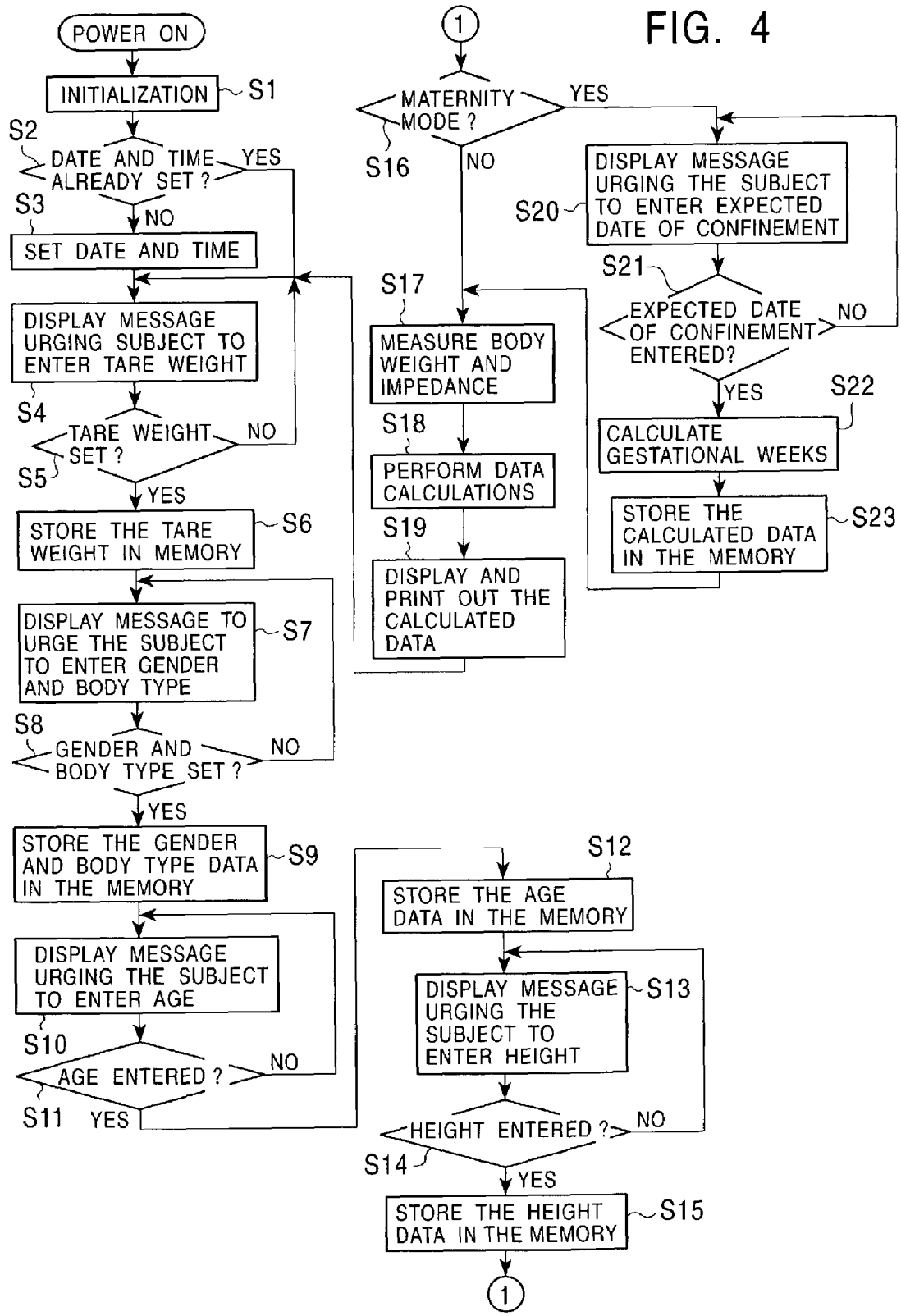
FIG. 4 is a flowchart of the first embodiment.

In addition to the determinations of the percent body fat and the total body fat indicated by FIGS. 8, 10, 11 and 12, the patient's BMI when she is not pregnant is entered at some point from STEP S7 to STEP S15 in FIG. 4, an amount of increase in body fat is calculated in STEP S18 in FIG. 4 for each group of weeks after conception for each body type based on the BMI of the subject when she is not pregnant as shown in FIG. 13, and when an amount of increase in the body fat of the patient in a certain week after conception exceeds a corresponding value in the table shown in FIG. 13, some advice can be displayed on the display section 8 or printed out in the print section 9. In this case, because the pregnant woman is obese and her total body fat must decrease after the 28$^{th}$ week after conception, advice urging the patient to decrease her total body fat is displayed and/or printed out if the total body fat does not decrease.

Figure 14:
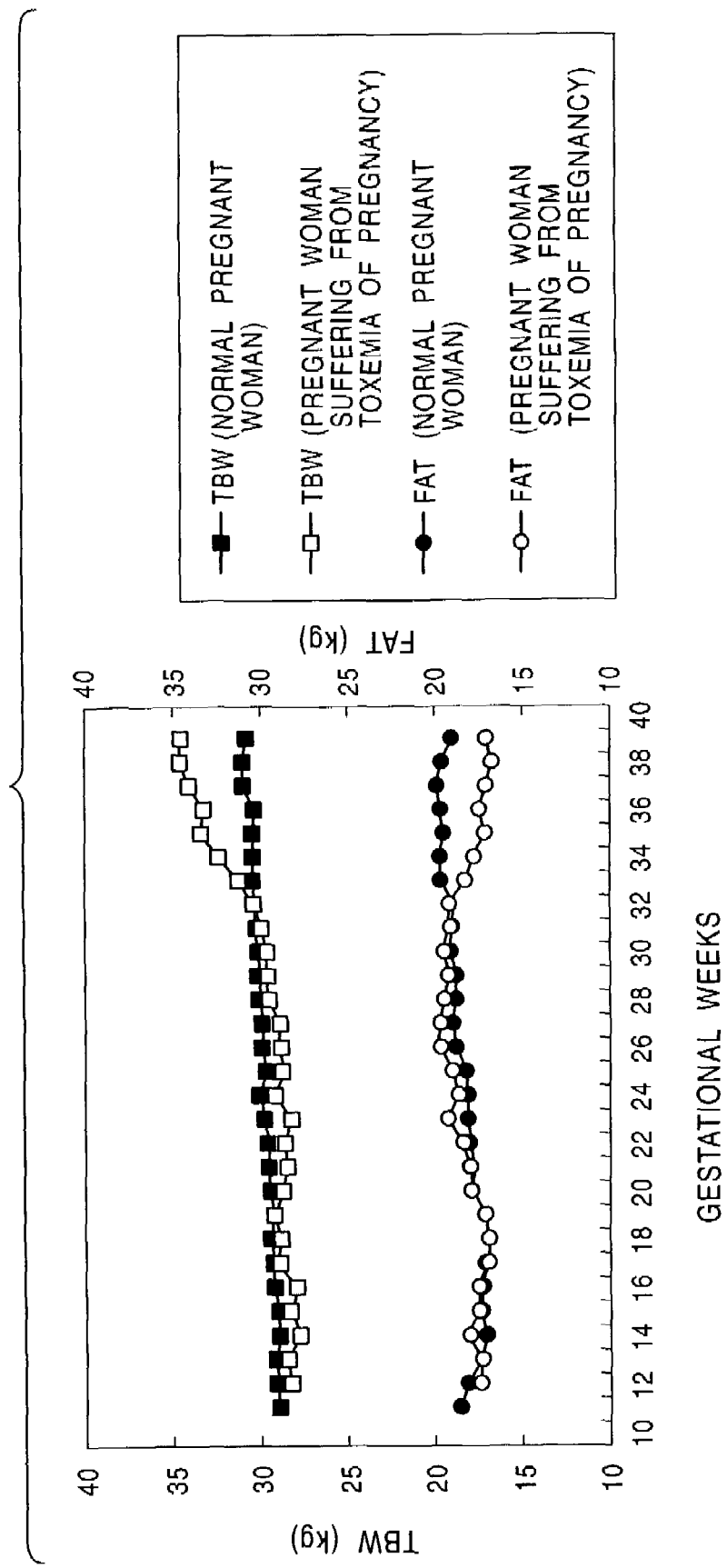
FIG. 14 is a diagram showing relationships between the gestational weeks and total body waters and relationships between the gestational weeks and total body fats.

Further, the total body water/total body fat ratio shows onset(s) of edema or/and toxemia of pregnancy of the pregnant woman at the time of measurement. As shown in FIG. 14, a total body water (indicated as "TBW" in the figure) of a pregnant woman (excluding a fetal part) with a normal body type tends to slightly increase as the gestational weeks increases, and a total body fat (indicated as "FAT" in the figure) of the pregnant woman tends to slightly increase as the gestational weeks increases but decrease to some degree in a late stage of pregnancy. However, once the pregnant woman develops edema or toxemia of pregnancy, the total body water sharply increases while the total body fat decreases.

Figure 15:
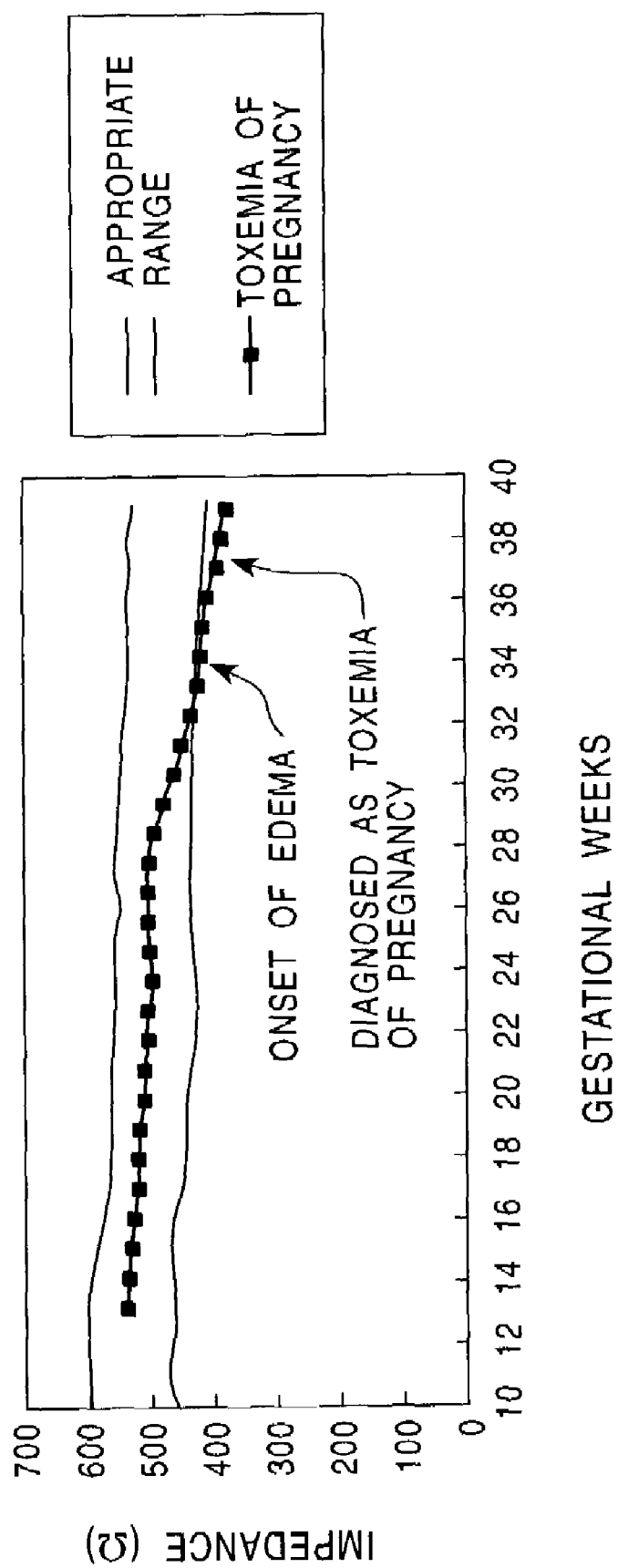
FIG. 15 is a diagram showing a relationship between the gestational weeks and a bioelectrical impedance.
Figure 16:
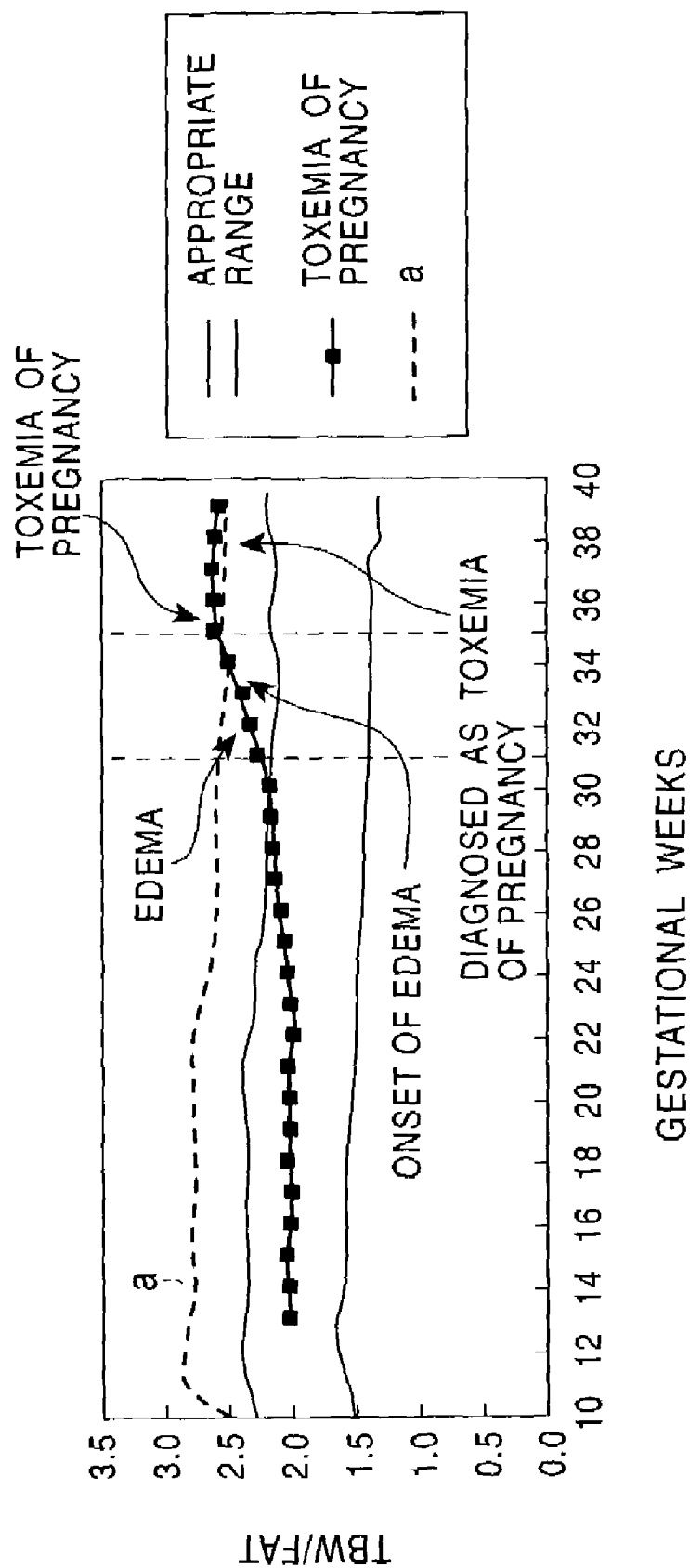
FIG. 16 is a diagram showing a relationship between the gestational weeks and a total body water/total body fat ratio.

As a result of examining this tendency meticulously, it has been found that when a pregnant woman of normal body type develops edema or toxemia of pregnancy, a bioelectrical impedance becomes lower than an appropriate range as shown in FIG. 15. Thereby, a total body water and a total body fat which are calculated based on the bioelectrical impedance change. Further, it has also been found that a value (TBW/FAT) obtained by dividing the total body water by the total body fat based on the bioelectrical impedance, as shown in FIG. 16, appears as a change in the body of the pregnant woman of normal body type and deviates from an appropriate range at least two weeks before a doctor examines the woman and finds the change. Hence, the appropriate range of the total body water/total body fat is determined according to the gestational weeks, a range above the appropriate range is defined as a range (above upper limits of the appropriate range or a range between the appropriate range and a graph a) in which edema develops, a range above the graph a is defined as a range in which toxemia of pregnancy develops, and these ranges are stored in the memory 18. Then, the result of the calculation performed in STEP S18 is compared with these ranges so as to display and print out whether edema or toxemia of pregnancy develops in STEP S19. The display and printout can be carried out at least two weeks earlier than the examination of the pregnant woman. Therefore, the pregnant woman can be subjected to proper treatment before onset of edema or toxemia of pregnancy.

For example, as shown in FIG. 16, when the result of the calculation exceeds an upper limit of the appropriate range, a message such as "There is a possibility that you will have edema. You should be careful about an excessive intake of water and keep an intake of salt at 7 to 8 grams or lower. Keep your feet high when you sleep." is displayed on the display section 8 or printed out in the print section 9. Similarly, when the result of the calculation exceeds the graph a, a message such as "There is a possibility that you may develop toxemia of pregnancy. You should consult a doctor." is displayed or printed out.

In addition, as measurement is made every day, the result of the calculation may exceed the above appropriate range or graph a temporarily.

In that case, a message such as "A faint sign of onset of edema is seen. Please take measurements every day." is displayed or printed out.

Figure 17:
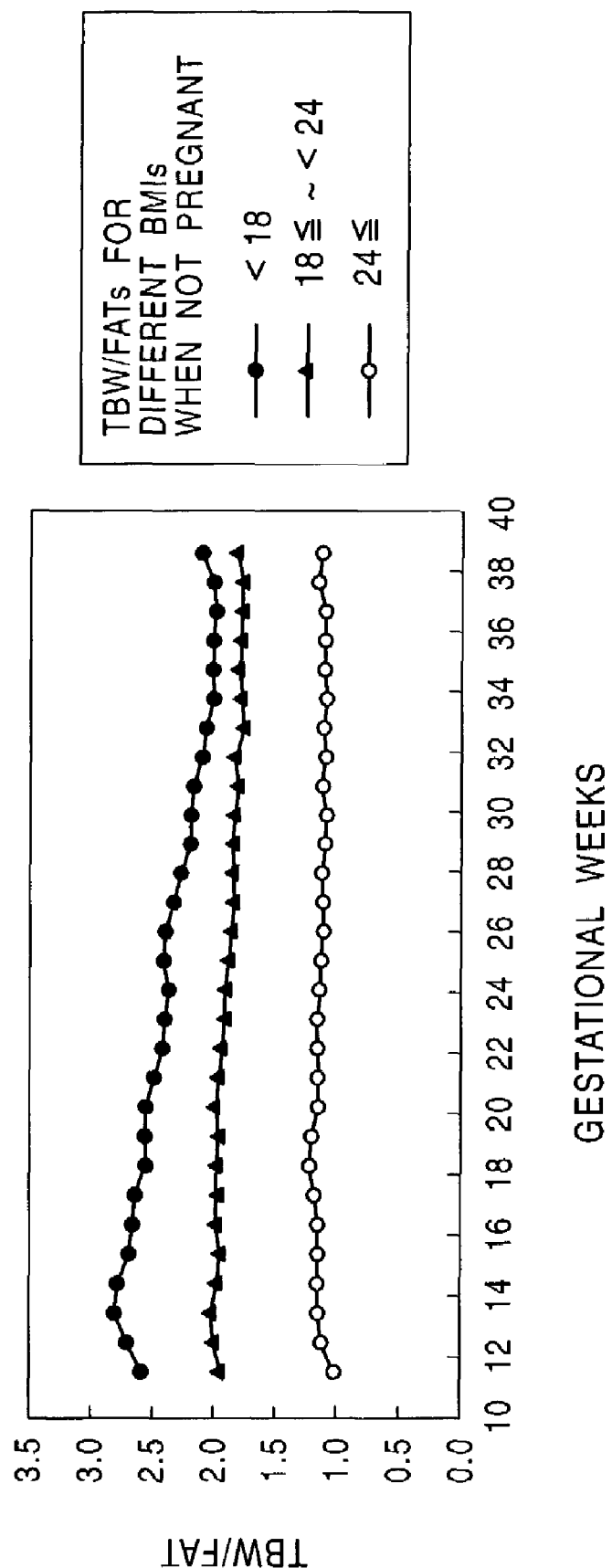
FIG. 17 is a diagram showing relationships between the gestational weeks and total body water/total body fat ratios for different BMIs of a pregnant woman when she is not pregnant.

The appropriate range shown in FIG. 16 varies according to a body type of the pregnant woman when she is not pregnant. Thus, to define the appropriate range for each possible body type of the pregnant woman when she is not pregnant, i.e., "slim" with a body mass index (BMI) of lower than 18, "normal" with a BMI of not lower than 18 and lower than 24 and "obese" with a BMI of not lower than 24, lines as shown in FIG. 17 may be defined as center lines of the appropriate ranges, and the appropriate ranges each may range a standard deviation of the corresponding center line±σ. These appropriate ranges can be changed accordingly according to levels of determinations of edema and toxemia of pregnancy.

Figure 18:
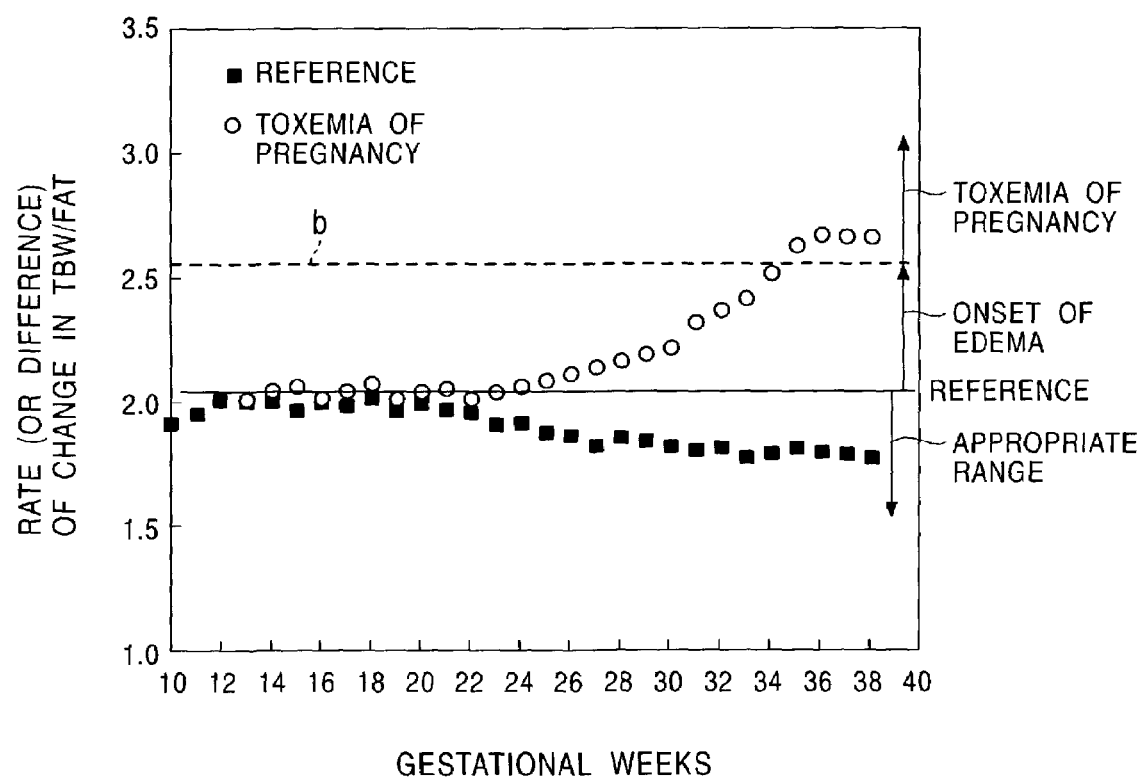
FIG. 18 is a diagram showing relationships between the gestational weeks and changes in total body water/total body fat ratios.

Further, in an early stage of pregnancy, morning sickness is apt to occur and a bioelectrical impedance is not stable. In addition, edema often appears from the $28^{th}$ week after conception. Hence, as shown in FIG. 18, using a total body water/total body fat (indicated as "TBW/FAT" in FIG. 18) value in the $20^{th}$ week after conception as a reference, onset of edema or toxemia of pregnancy may be determined based on a rate of change from the reference value. The above reference value is not limited to the value in the $20^{th}$ week after conception, and use of a value in a week in which the bioelectrical impedance is stable leads to accurate determinations of onsets of edema and toxemia of pregnancy. In this case as well, a result of calculation may go too far in a positive direction or exceed a graph b temporarily. In that case, a message such as "A faint sign of onset of edema is seen. Please take measurements every day." is displayed or printed out.

Furthermore, to further improve accuracy, by use of the result of the determination of the total body water/total body fat based on FIG. 16 and the result of the determination of the rate of change based on FIG. 18, the physical condition of the pregnant woman is determined based on a matrix shown in FIG. 19 in which "0" indicates "No edema is found. Your physical condition is normal.", "1" indicates "Edema (+): Please be careful about onset of edema. You should review your life style and dietary life.", "2" indicates "Edema (++): Edema is seen. Please be careful about toxemia of pregnancy.", "3" indicates "Edema (+++): Edema is clearly seen. Onset of toxemia of pregnancy is suspected." and "4" indicates "Edema (++++): Edema is being worsened. Onset of toxemia of pregnancy is strongly suspected." One of these messages is displayed on the display section 8 or printed out in the print section 9 according to the determined physical condition of the pregnant woman. The determination in this case is such that when the physical condition of the pregnant woman is indicated by the same cell in the matrix over a number of successive days, a message corresponding to the cell is displayed or printed, and even if her physical condition is indicated by a different cell temporarily, a message corresponding to the last cell is displayed or printed out.

Next, a second embodiment of the present invention in a case where, in particular, the system 1 is used as the health care system will be described.

Figure 9:
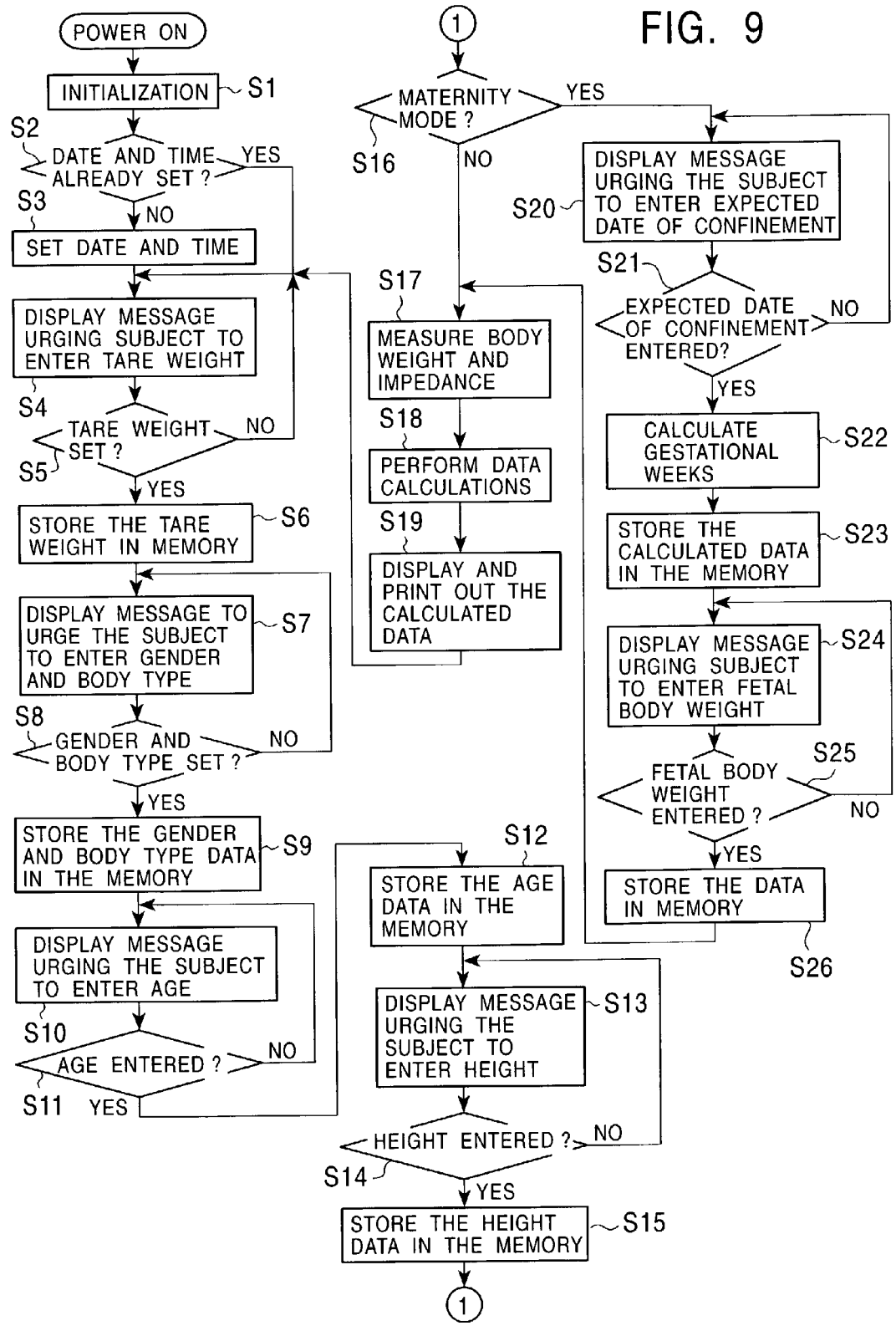
FIG. 9 is a flowchart of a second embodiment.

A constitution and electric block diagram of the second embodiment are the same as those shown in FIGS. 1 and 3 of the first embodiment. A flowchart shown in FIG. 9 of the second embodiment is the same as that shown in FIG. 4 except that STEPS S24, S25 and S26 are newly added after STEP S23. In the present embodiment, unlike the first embodiment in which a fetal body weight which constitutes a weight of a fetal part in conjunction with a weight of an amniotic fluid and a weight of a placenta is estimated according to the gestational weeks in FIG. 6 and input automatically, a fetal body weight value estimated by ultrasonotomography is manually input by use of the numeric keypad in STEP S25, stored in the memory 18, and then used in computations performed in STEP S18. Otherwise, the second embodiment is the same as the first embodiment.

In the present invention, a weight of a fetal part comprising a fetal body weight, a weight of an amniotic fluid and a weight of a placenta according to the gestational weeks is stored in the memory, and computations are performed based on the stored data. However, these data may be entered in numerics by use of the numeric keypad each time measurement is made.

Further, a body weight before a weight of a fetal part is subtracted therefrom and the weight of the fetal part can also be entered by use of the numeric keypad. In that case, the present invention can also be applied to a hand type body fat measuring device or card-type body fat measuring device incorporating no weighing machine.

In addition, in the above embodiment, the results of the computations are displayed and printed out. However, they can be expressed as graphs as shown in FIGS. 16 and 18 together with past data read from the memory 18.

Further, in the above embodiment, a total body weight and a total body fat are computed by use of a corrected body weight excluding a weight of a fetal part. The computations are not limited to use of the corrected body weight, and it has also been found that results of computations performed by using a measured body weight as it is show similar tendencies. Therefore, the computations may be preformed by use of the pre-correction body weight.

Next, a second embodiment of the present invention in a case where, in particular, the system 1 is used as the percent body fat measuring system will be described. A constitution and electric block diagram of the second embodiment are the same as those shown in FIGS. 1 and 3 of the first embodiment. A flowchart shown in FIG. 9 of the second embodiment is the same as that shown in FIG. 4 except that STEPS S24, S25 and S26 are newly added after STEP S23. In the present embodiment, unlike the first embodiment in which a fetal body weight which constitutes a weight of a fetal part in conjunction with a weight of an amniotic fluid and a weight of a placenta is estimated according to the gestational weeks in FIG. 6 and input automatically, a fetal body weight value estimated by ultrasonotomography is manually input by use of the numeric keypad in STEP S25, stored in the memory 18, and then used in computations performed in STEP S18. Illustrative examples of a method of determining a fetal body weight by the ultrasonotomography include an Osaka University method using three parameters measured by ultrasound, i.e., a biparietal diameter of a fetal head, an area of a fetal trunk and a length of a fetal thigh bone and a Tokyo University method using a circumference of a fetal trunk and an occipitofrontal diameter thereof. In this case, a weight of an amniotic fluid and a weight of a placenta are entered automatically based on a corresponding gestational weeks in FIG. 6.

To determine a percent body fat or a total body fat in the present second embodiment, they can be determined in the same manner as in the first embodiment by use of graphs obtained by substituting the gestational weeks on horizontal axes in FIGS. 8, 10 and 12 of the first embodiment with fetal body weights estimated by the ultrasonotomography. Otherwise, the second embodiment is the same as the first embodiment.

Further, it is also possible to determine a fetal body weight by the ultrasonotomography and determine a weight of an amniotic fluid and a weight of a placenta from the fetal body weight. In addition, when the weight of the amniotic fluid is also determined by the known ultrasonotomography, a weight of an amniotic fluid of a pregnant woman suffering from hydramnios or oligoamnios can be determined accurately.

Figure 20:
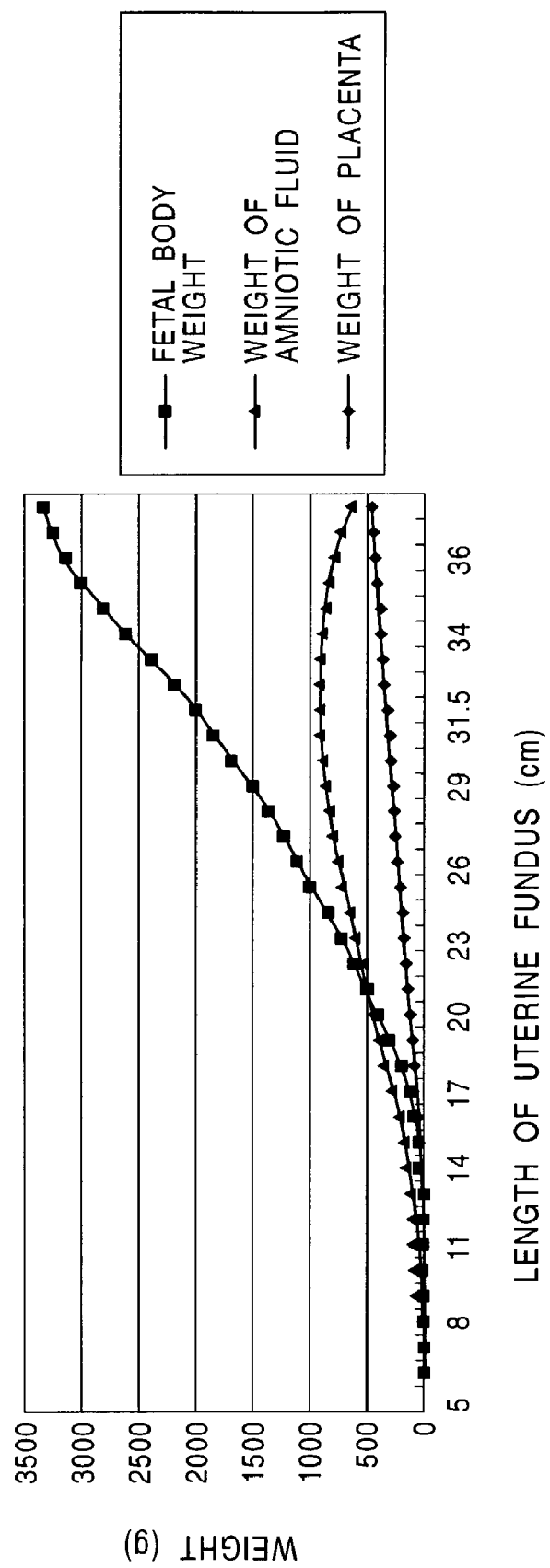
FIG. 20 is a diagram showing a relationship between a length of uterine fundus and a weight of a fetal part.

Next, a third embodiment of the present invention in a case where, in particular, the system 1 is used as the percent body fat measuring system will be described. The present inventors have paid attention to a fact that a length of uterine fundus (length of an anterior abdominal wall from an upper edge of pubic symphysis to uterine fundus) increases as the gestational weeks increases and have found that a fetal body weight, a weight of an amniotic fluid and a weight of a placenta have certain relationships with the length of uterine fundus as shown in FIG. 20. In the third embodiment, a length of uterine fundus is entered after STEP S23 in FIG. 4 of the first embodiment, and a weight of a fetal part (total of a fetal body weight, a weight of an amniotic fluid and a weight of a placenta) is computed based on FIG. 20 in performing the computations in STEP S18 so as to determine a percent body fat, a total body fat, a fat-free body weight and a total body water as in the case of the first embodiment. To determine a percent body fat or a total body fat in the present third embodiment, they can be determined in the same manner as in the first embodiment by use of graphs obtained by substituting the gestational weeks on horizontal axes in FIGS. 8, 10 and 12 of the first embodiment with lengths of uterine fundus. Otherwise, the third embodiment is the same as the first embodiment.

Figure 21:
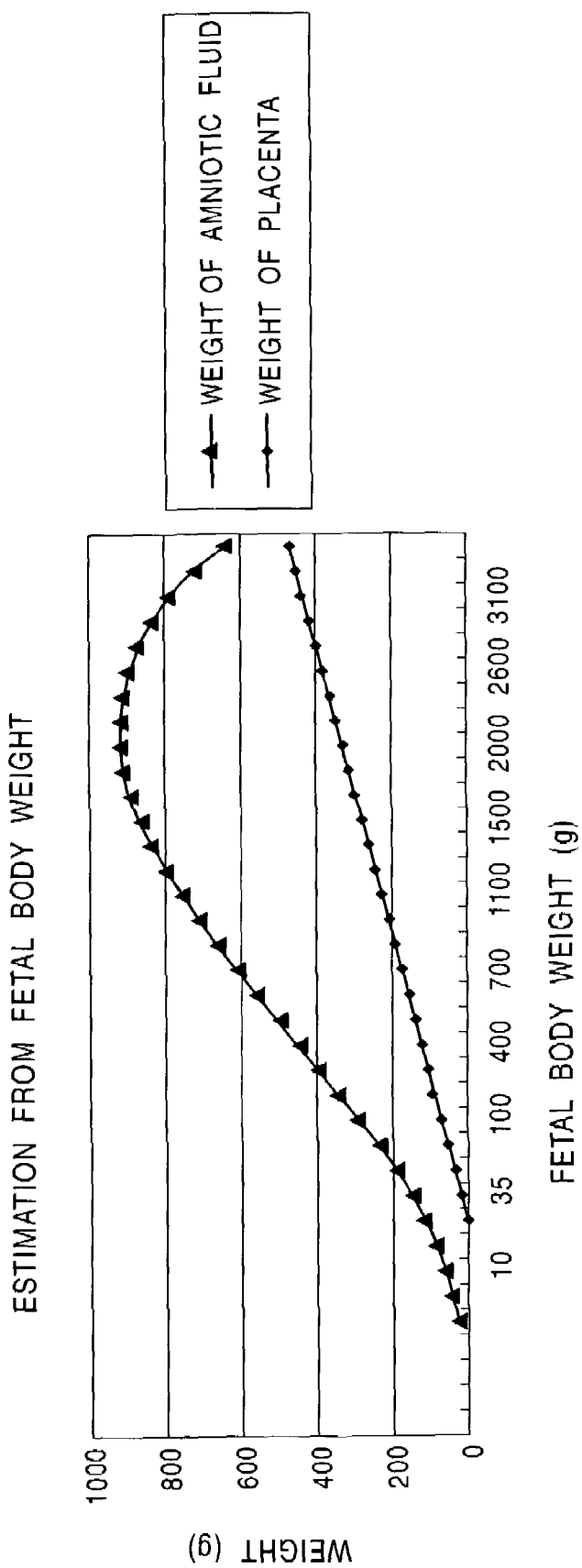
FIG. 21 is a diagram showing a relationship between a weight of an amniotic fluid and a fetal body weight and a relationship between a weight of a placenta and the fetal body weight.

Further, it has been found that a weight of an amniotic fluid and a weight of a placenta have relationships shown in FIG. 21 with a fetal body weight. Therefore, in the third embodiment, it is also possible to determine only a fetal body weight from a length of uterine fundus by use of FIG. 14 and determine a weight of an amniotic fluid and a weight of a placenta from the determined fetal body weight by use of FIG. 15 so as to determine a weight of a fetal part which is a total of these weights.

Further, in the third embodiment, it is also possible to determine only a fetal body weight from a length of uterine fundus by use of FIG. 14 and determine a weight of an amniotic fluid and a weight of a placenta from the gestational weeks by use of FIG. 6 so as to determine a weight of a fetal part which is a total of these weights.

In the present invention, a weight of a fetal part comprising a fetal body weight, a weight of an amniotic fluid and a weight of a placenta according to the gestational weeks is stored in the memory, and computations are performed based on the stored data. However, these data may be entered in numerics by use of the numeric keypad each time measurement is made.

Further, a body weight before a weight of a fetal part is subtracted therefrom and the weight of the fetal part can also be entered by use of the numeric keypad. In that case, the present invention can also be applied to a manual adipometer or card-type adipometer incorporating no weighing machine.

In addition, in the above embodiments, the results of the computations are displayed and printed out. However, the results of the computations can be expressed as graphs as shown in FIGS. 8, 10, 11 and 12 together with past data read from the memory 18 so as to show changes in the past.

Figure 22:
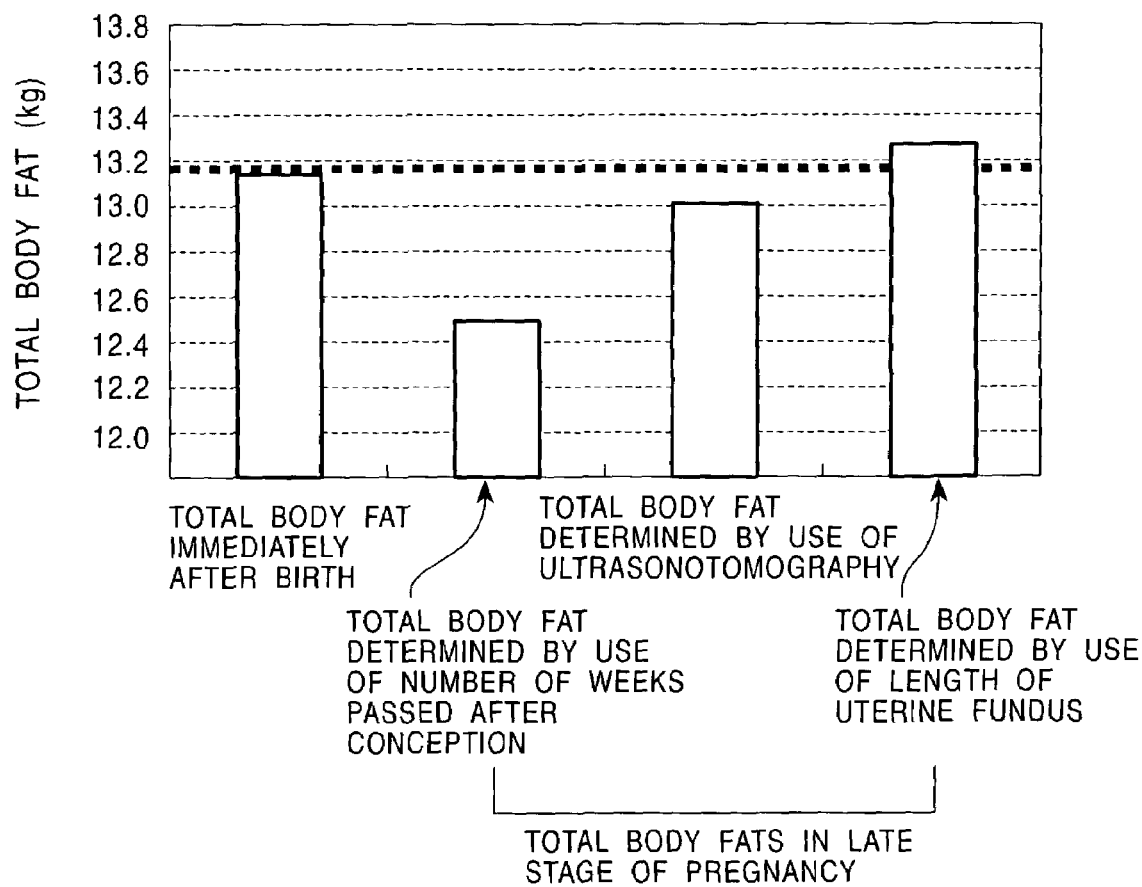
FIG. 22 is a diagram showing relationships between total body fats calculated by use of the gestational weeks, ultrasonotomography and a length of uterine fundus and a total body fat immediately after birth which is measured by use of a conventional adipometer.

In the above embodiments, a weight of a fetal part is determined from the gestational weeks, ultrasonotomography or a length of uterine fundus so as to determine a percent body fat and a total body fat. Examining results by these methods, they can be expressed as shown in FIG. 22. These results are examined on an assumption that a total body fat immediately after birth (indicated as "after birth") is nearly the same as that in a late stage of pregnancy. According to the assumption, a total body fat when the gestational weeks (indicated as "number of weeks") is used is somewhat smaller than the measurement result after birth, a total body fat when ultrasonotomography (indicated as "ultrasound") is used is almost the same as the measurement result after birth, and a total body fat when a length of uterine fundus is used is slightly larger than the measurement result after birth. Thereby, it is understood that any two of the gestational weeks, the ultrasonotomography and the length of uterine fundus, e.g., a combination of the gestational weeks and the ultrasonotomography, a combination of the gestational weeks and the length of uterine fundus and a combination of the length of uterine fundus and the ultrasonotomography, or all three of them can be used in combination so as to determine a weight of a fetal part. When any two or three of these are used in combination, accuracy further improves and errors in fetal part weight measurement caused by variations in growth of a fetus ascribable to constitution and physical condition of a pregnant woman can be decreased.

The present invention is a system for measuring a percent body fat or total body fat of a pregnant woman by a bioelectrical impedance method, which comprises first input means, second input means and computation means, wherein personal data of a subject such as a height and a body weight is input into the first input means, a weight of a fetal part is input into the second input means, and the computation means computes a percent body fat or total body fat by subtracting the body weight input into the second input means from the body weight input into the first input means. Thereby, a pregnant woman can measure her percent body fat or total body fat with ease.

Further, the present invention is a system for measuring a percent body fat or total body fat of a pregnant woman by a bioelectrical impedance method, which comprises first input means, second input means, computation means and determination means, wherein personal data of a subject such as a height and a body weight is input into the first input means, a weight of a fetal part is input into the second input means, the computation means computes a percent body fat or total body fat by subtracting the body weight input into the second input means from the body weight input into the first input means, and the determination means determines the percent body fat or total body fat based on the gestational weeks, ultrasonotomography or a length of uterine fundus. Thereby, a pregnant woman can measure her percent body fat or total body fat with ease and also determine the percent body fat or total body fat based on the gestational weeks, ultrasonotomography or a length of uterine fundus.

Also, the present invention is a health care system for a pregnant woman, which comprises input means, computation means, reference setting means, comparison means and determination means, wherein personal data of a pregnant woman such as a height and a body weight is input into the input means, the computation means computes a total body water and a total body fat by a bioelectrical impedance method, the reference setting means has reference values corresponding to a specific week after conception, the comparison means compares the results of the computations performed by the computation means with the reference values, and the determination means determines a physical condition of the pregnant woman based on the results of the comparisons made by the comparison means. Thereby, health care administration including treatments for avoiding onsets of edema and toxemia of pregnancy of a pregnant woman can be performed objectively and quantitatively.

Further, the present invention is a health care system for a pregnant woman, which comprises input means, computation means, reference setting means, comparison means and determination means, wherein personal data of a pregnant woman such as a height and a body weight is input into the input means, the computation means computes a ratio of a total body water to a total body fat by a bioelectrical impedance method, the reference setting means has a reference ratio value corresponding to a specific week after conception, the comparison means compares a rate of change from the ratio computed by the computation means with the reference ratio value, and the determination means determines a physical condition of the pregnant woman based on the result of the comparison made by the comparison means. Thereby, health care administration including treatments for avoiding onsets of edema and toxemia of pregnancy of a pregnant woman can be performed objectively and quantitatively.

Further, the present invention displays advice about health of a pregnant woman. Therefore, it is useful and convenient for pregnant women.

In addition, the present invention computes a total body water and a total body fat based on a bioelectrical impedance between feet of a pregnant woman and can detect onset of edema or toxemia of pregnancy in its early stage by measuring lower limbs where edema is apt to appear.

Furthermore, the present invention uses, as a reference ratio value, a ratio value in a week after conception in which a bioelectrical impedance of a pregnant woman is stable. Therefore, accurate determination can be made.

What is claimed is:

1. A system for measuring a percent body fat of a pregnant woman, the system comprising:
    means for measuring a bioelectrical impedance;
    first input means for receiving personal data of a patient,
    second input means for receiving a weight of a fetal part, and
    computation means for subtracting the body weight input into the second input means from a body weight input into the first input means to yield a subtraction result, and for computing a percent body fat based on the subtraction result and the measured bioelectrical impedance.

2. The system of claim 1, wherein the weight of the fetal part is determined from the gestational weeks.

3. The system of claim 1, wherein the weight of the fetal part is determined from a length of uterine fundus.

4. The system of claim 1, wherein the weight of the fetal part is determined by ultrasonotomography.

5. The system of claim 1, wherein the weight of the fetal part is determined from the gestational weeks and a length of uterine fundus.

6. The system of claim 1, wherein the weight of the fetal part is determined from the gestational weeks and ultrasonotomography.

7. The system of claim 1, wherein the weight of the fetal part is determined from a length of uterine fundus and ultrasonotomography.

8. The system of claim 1, wherein the weight of the fetal part comprises a fetal body weight, a weight of an amniotic fluid and a weight of a placenta.

9. A system for measuring a total body fat of a pregnant woman, the system comprising:
    means for measuring a bioelectrical impedance;
    first input means for receiving personal data of a patient,
    second input means for receiving a weight of a fetal part, and
    computation means for subtracting the body weight input into the second input means from a body weight input into the first input means to yield a subtraction result, and for computing a total body fat based on the subtraction result and the measured bioelectrical impedance.

10. A system for measuring a percent body fat of a pregnant woman, the system comprising:
    means for measuring a bioelectrical impedance;
    first input means for receiving personal data of a patient,
    second input means for receiving a weight of a fetal part,
    computation means for subtracting the body weight input into the second input means from a body weight input into the first input means to yield a subtraction result, and
    determination means for determining the percent body fat based on gestational weeks, the subtraction result, and the measured bioelectrical impedance.

11. A system for measuring a total body fat of a pregnant woman, the system comprising:
    means for measuring a bioelectrical impedance;
    first input means for receiving personal data of a patient,
    second input means for receiving a weight of a fetal part,
    computation means for subtracting the body weight input into the second input means from a body weight input into the first input means to yield a subtraction result, and
    determination means for determining the total body fat based on gestational weeks, the subtraction result, and the measured bioelectrical impedance.

12. A system for measuring a percent body fat of a pregnant woman, the system comprising:
    means for measuring a bioelectrical impedance;
    first input means for receiving personal data of a patient,
    second input means for receiving a weight of a fetal part,
    computation means for subtracting the body weight input into the second input means from a body weight input into the first input means to yield a subtraction result, and
    determination means for determining the percent body fat based on a length of uterine fundus, the subtraction result, and the measured bioelectrical impedance.

13. A system for measuring a total body fat of a pregnant woman, the system comprising:
    means for measuring a bioelectrical impedance;

a first input means for receiving personal data of a patient, a second input means for receiving a weight of a fetal part, computation means for subtracting the body weight input into the second input means from a body weight input into the first input means to yield a subtraction result, and determination means for determining the total body fat based on a length of uterine fundus, the subtraction result, and the measured bioelectrical impedance.

14. A system for measuring a percent body fat of a pregnant woman, the system comprising:

means for measuring a bioelectrical impedance;

first input means for receiving personal data of a patient, second input means for receiving a weight of a fetal part, computation means for subtracting the body weight input into the second input means from a body weight input into the first input means to yield a subtraction result, and determination means for determining the percent body fat based on a fetal body weight, the subtraction result, and the measured bioelectrical impedance.

15. A system for measuring a total body fat of a pregnant woman, the system comprising:

means for measuring a bioelectrical impedance;

first input means for receiving personal data of a patient, second input means for receiving a weight of a fetal part, computation means for subtracting the body weight input into the second input means from a body weight input into the first input means to yield a subtraction result, and determination means for determining the total body fat based on a fetal body weight, the subtraction result, and the measured bioelectrical impedance.

16. A health care system for a pregnant woman, comprising:

input means for receiving personal data of a pregnant woman, computation means for computing a total body water and a total body fat by a bioelectrical impedance measurement wherein a current is applied through a body, a resulting voltage is measured, and the impedance is calculated based on a relationship between the current and the voltage, reference setting means having reference values corresponding to a specific week after conception, comparison means for comparing the results of the computations performed by the computation means with the reference values, and determination means for determining a physical condition of the pregnant woman based on the results of the comparisons made by the comparison means;

wherein the determination means determines onset of edema.

17. A health care system for a pregnant woman, comprising:

input means for receiving personal data of a pregnant woman, computation means for computing a total body water and a total body fat by a bioelectrical impedance measurement wherein a current is applied through a body, a resulting voltage is measured, and the impedance is calculated based on a relationship between the current and the voltage, reference setting means having reference values corresponding to a specific week after conception, comparison means for comparing the results of the computations performed by the computation means with the reference values, and determination means for determining a physical condition of the pregnant woman based on the results of the comparisons made by the comparison means;

wherein the determination means determines onset of toxemia of pregnancy.

18. A health care system for a pregnant woman, comprising:

input means for receiving personal data of a pregnant woman, computation means for computing a total body water and a total body fat by a bioelectrical impedance measurement wherein a current is applied through a body, a resulting voltage is measured, and the impedance is calculated based on a relationship between the current and the voltage, reference setting means having reference values corresponding to a specific week after conception, comparison means for comparing the results of the computations performed by the computation means with the reference values, and determination means for determining a physical condition of the pregnant woman based on the results of the comparisons made by the comparison means;

wherein the determination means determines onsets of edema and toxemia of pregnancy.

19. A health care system for a pregnant woman, comprising:

input means for receiving personal data of a pregnant woman, computation means for computing a total body water and a total body fat by a bioelectrical impedance measurement wherein a current is applied through a body, a resulting voltage is measured, and the impedance is calculated based on a relationship between the current and the voltage, reference setting means having reference values corresponding to a specific week after conception, comparison means for comparing the results of the computations performed by the computation means with the reference values, and determination means for determining a physical condition of the pregnant woman based on the results of the comparisons made by the comparison means;

wherein the determination means displays advice about health of the pregnant woman.

20. A health care system for a pregnant woman comprising:

input means for receiving personal data of a pregnant woman, computation means for computing a total body water and a total body fat by a bioelectrical impedance measurement wherein a current is applied through a body, a resulting voltage is measured, and the impedance is calculated based on a relationship between the current and the voltage, reference setting means having reference values corresponding to a specific week after conception, comparison means for comparing the results of the computations performed by the computation means with the reference values, and determination means for determining a physical condition of the pregnant woman based on the results of the comparisons made by the comparison means;

wherein the computation means computes the total body water and the total body fat based on a bioelectrical impedance between feet of the pregnant woman.

21. A health care system for a pregnant woman, comprising:

input means for receiving personal data of the pregnant woman, computation means for computing a ratio of a total body water to a total body fat by a bioelectrical impedance measurement wherein a current is applied through a body, a resulting voltage is measured, and the impedance is calculated based on a relationship between the current and the voltage, reference setting means having a reference ratio value corresponding to a specific week after conception, comparison means for comparing a rate of change from the ratio computed by the computation means with the reference ratio value, and determination means for determining a physical condition of the pregnant woman based on the result of the comparison made by the comparison means.

22. The system of claim 21, wherein the determination means determines onset of edema when the computed ratio is larger than the reference ratio value.

23. The system of claim 21, wherein the determination means determines onset of toxemia of pregnancy when the computed ratio is larger than the reference ratio value.

24. The system of claim 21, wherein the determination means determines onsets of edema and toxemia of pregnancy when the computed ratio is larger than the reference ratio value.

25. The system of claim 21, wherein the determination means displays advice about health of the pregnant woman.

26. The system of claim 21, wherein the computation means computes the total body water and the total body fat based on a bioelectrical impedance between feet of the pregnant woman.

27. The system of claim 21, wherein the reference setting means uses, as the reference ratio value, a ratio value corresponding to a specific week after conception during which the bioelectrical impedance of the pregnant woman is stable.

* * * * *